United States Patent [19]
Critser et al.

[11] Patent Number: 5,753,427
[45] Date of Patent: *May 19, 1998

[54] GENERAL METHOD TO QUICKLY ADD CRYOPROTECTANTS TO ANIMAL CELLS WHILE MAINTAINING VIABILITY

[75] Inventors: John K. Critser, Carmel; Dayong Gao, Indianapolis, both of Ind.

[73] Assignee: Methodist Hospital of Indiana, Indianapolis, Ind.

[ * ] Notice: The term of this patent shall not extend beyond the expiration date of Pat. No. 5,691,133.

[21] Appl. No.: 478,873

[22] Filed: Jun. 7, 1995

Related U.S. Application Data

[63] Continuation-in-part of Ser. No. 250,675, May 27, 1994, Pat. No. 5,595,866.

[51] Int. Cl.$^6$ .............................................. A01N 1/02
[52] U.S. Cl. ................................... 435/2; 435/1.3
[58] Field of Search .......................... 435/1.3, 2

[56] References Cited

U.S. PATENT DOCUMENTS

| | | | |
|---|---|---|---|
| 4,429,542 | 2/1984 | Sankao et al. | 62/62 |
| 4,464,337 | 8/1984 | Zelman | 422/41 |
| 4,965,186 | 10/1990 | Grischenko et al. | 435/2 |
| 4,980,277 | 12/1990 | Junnila | 435/2 |
| 5,026,342 | 6/1991 | Hammerstedt et al. | 600/35 |
| 5,261,870 | 11/1993 | Hammerstedt et al. | 600/35 |

OTHER PUBLICATIONS

Fertility & Sterility, vol. 14, No. 1, issued 1963, J.K. Sherman, "Improved Methods of Preservation of Human Spermatozoa by Freezing and Freeze–Drying", pp. 49–64.

Acta Vet. Scand., vol. 32, No. 4, issued 1991, C.O. Bwanga, "Cryopreservation of Boar Sperm", pp. 431–453.

Cryobiology, vol. 26, issued 1989, Fiser et al., "The Effect of Glycerol–Related Osmotic Changes on Post–Thaw Motility and Acrosomal Integrity of Ram Spermatozoa", pp. 64–69.

Cryobiology, vol. 29, issued 1992, Gao et al., "Glycerol Permeability of Human Spermatozoa and its Activation Energy", pp. 657–667.

Biology of Reproduction, vol. 49, issued 1993, Gao et al., "Hyperosmotic Tolerance of Human Spermatozoa: Seperate Efects on Glycerol, Sodium Chloride, and Sucrose on Spermolysis", pp. 112–123.

The American Fertility Society and Methodist Hospital of Indiana, Inc. in cooperation with the Reproductive Biology Special Interest Group, Critser et al., "Advanced Hands–On Workshop on Cryopreservation of Spermatozoa and Embryos", Postgraduate course at Methodist Hospital of Indiana, Indianapolis, IN on 11–13 Jun. 1993, mailed to participants no earlier than 01 Jun. 1993.

O. Kedem & A. Katchalsky, Thermodynamic Analysis of the Permeability of Biological Membranes to Non–Electrolytes, vol. 27 (1958), Biochimica Et Biophysica ACTA.

Junying Du, F.W. Kleinhans, P. Mazur and J.K. Critser, Osmotic Behavior of Human Spermatozoa Studied by EPR, Cryo–Letters 14, 285–294 (1993).

E.E. Noiles, P. Mazur, P.F. Watson, F.W. Kleinhans, and J. K. Critser, "Determination of Water Permeability Coefficient for Human Spermatozoa and its Activation Energy", Biology of Reproduction, 48, 99–109 (1993).

*Primary Examiner*—Sandra E. Saucier
*Attorney, Agent, or Firm*—Woodard, Emhardt, Naughton, Moriarty & McNett

[57] ABSTRACT

A mathematical model, and membranes and devices based upon that model, to optimize protocols for the addition or removal of cryoprotectant to or from biological cells. This disclosure describes the use of four equations to predict optimal protocols to add or remove cryoprotectant to or from biological cells. The equations particularly require experimentally found data, specific to cell-type and species, regarding the osmotic tolerance of the cells, where osmotic tolerance refers to the cells ability to shrink or swell to various changes in osmolality without injury. The equations further require the cryoprotectant permeability coefficient and the water permeability coefficient of the particular cells' plasma membrane. These coefficients are found with experimental data of the knetic volume change of the cell-type to a known concentration and temperature of cryoprotectant. Also disclosed are particularly preferred methods and devices to add or remove cryoprotectant to or from these cells based upon these equations.

28 Claims, 36 Drawing Sheets

- ■ : 250 mOsm
- ○ : 230 mOsm
- ● : 190 mOsm
- ▽ : 143 mOsm
- ▼ : 114 mOsm
- □ : 90 mOsm a: 0.5M glycerol
b: 1M glycerol
c: 1.5M glycerol
d: 2M glycerol 1: ORIGINAL SPERM IN 1M GLYCEROL
2: ONE-STEP RETURNED TO ISOTONIC MEDIUM
3: 8-STEP RETURNED TO ISOTONIC MEDIUM (FIXED-MOLARITY)
4: 8-STEP RETURNED TO ISOTONIC MEDIUM (FIXED VOLUME)
5: 2-STEP RETURNED TO ISOTONIC MEDIUM USING SUCROSE AS AN OSMOTIC BUFFER.

GENERAL METHOD TO QUICKLY ADD CRYOPROTECTANTS TO ANIMAL CELLS WHILE MAINTAINING VIABILITY

This is a continuation-in-part of prior U.S. application Ser. No. 08/250,675, filed May 27, 1994, now U.S. Pat. No. 5,595,866.

This invention was made with the support by one or more grants from the National Institute of Health of the United States of America. The Government of the United States has certain rights in the invention.

BACKGROUND OF THE INVENTION

Fresh biological cells such as sperm, blood, or pancreatic islet cells are viable for a relatively short period of time before they spoil and must be destroyed. Nevertheless, it is often advantageous to use such biological material long after it has been collected, sometimes several months or even years later. Various methods, principally freezing, are employed, where known possible, to preserve biological cells for these relatively longer periods of time. For example, freezing sperm permits a domestic animal breeder to maintain stocks of valuable sperm for use when necessary, enables the inexpensive transport of such stocks, and ultimately permits genetically superior males to inseminate a larger number of females. Beyond livestock, artificial insemination is also used in the human context for various medical and health reasons. As another example, freezing blood permits blood donations to last much longer than the typical 14 day storage period. Moreover, diseases carried in blood with a latency period longer than 14 days may not be discovered in the donor until the blood has been placed into a patient. Frozen blood could exceed this period and allow donors to be screened beyond their date of donation.

The survivability of viable cells using prior art freezing methods is often quite low. Freezing conditions are relatively harsh and thermal shock or other phenomena such as ice crystal formation often destroy biological cells. Therefore, maximizing the viability of thawed cells has been the goal of many researchers.

The prior art discloses various methods for improving the survivability of frozen cells. U.S. Pat. No. 4,007,087 to Ericsson discloses a sperm fractionation and storage method which claims to increase the percentage of motile sperm that survive frozen storage. Ericsson discloses a method whereby motile sperm are separated from non-motile, defective or dead sperm. The fraction containing the motile sperm is then frozen. Ericsson reports that his method increases the fertility of a sperm sample by enhancing the environmental (the ratio of total sperm to motile sperm) and viability (progressiveness of motility of the motile sperm) factors effecting the fertility of a sample, but his method does not improve the population (motile sperm count) factor which is possibly the most critical.

U.S. Pat. No. 3,791,384 to Richter et al. discloses a method for deep freezing and thawing boar sperm which includes inactivating the fresh sperm by means of an inactivating solution that includes dextrose, dihydrate of ethleneditrotetra-acetic acid, sodium citrate and sodium hydrogencarbonate. Richter reports that inactivation of the sperm gives them a greater power of resistance to freezing.

U.S. Pat. No. 4,429,542 to Sakao et al., U.S. Pat. No. 4,487,033 to Sakao et al., U.S. Pat. No. 3,893,308 to Barkay et al. and U.S. Pat. No. 4,480,682 to Kameta et al. all disclose different freezing methods which claim to improve the fertility of sperm samples. In all of these methods, the temperature of sperm in solution is lowered by various means which attempt to reduce the thermal shock and increase the survivability of the viable sperm and ova present. Most of these methods are, however, complex, cumbersome and expensive to utilize. Other freezing methods are also used including the "Sherman" method of rapid freezing in liquid nitrogen vapors (Sherman, J. K., Improved Methods of Preservation of Human Spermatozoa by Freezing and Freeze Drying, Fertil. Steril., 14:49–64 (1963), and the "Behrman-Sanada" method of gradual freezing (Behrman et al. Meterologous and Humologus Inseminations with Human Semen Frozen and Stored in a Liquid Nitrogen Refrigerator., Fertil. Steril. 17:457–466 (1966)).

A disadvantage of the aforementioned methods resides in that low-temperature preservation of the cells is accompanied by the ice crystallization process. The ice crystallization process is retarded by the use of a cryoprotectant; however, the influence of the cryoprotectant on reducing ice crystallization is offset by the negative effects of the cryoprotectant on the cells. Addition of a cryoprotectant typically results in injury to the cell membrane because the addition leads to powerful osmotic shifts. The osmotic shifts cause partial denaturation of the protein molecules and disorientation of the cell organelles. In addition, if the cells have prolonged exposure to a high concentration of cryoprotectant before freezing, there is also concern that the cryoprotectant will be toxic to the cells. Accordingly, custom methods and devices are needed to rapidly add and remove a cryoprotective agent (CPA) as quickly as the membrane of a particular cell type will allow to avoid toxic effects and to shorten the time period from thawing to use while still maintaining the viability of the cells. The present invention addresses this need.

SUMMARY OF THE INVENTION

One aspect of this invention is a method to predict appropriate protocols to remove cryoprotectant from biological cells based on the cells' upper volume limit, the cell membrane's cryoprotectant permeability coefficient, and the cell membrane's water permeability coefficient.

A second aspect of this invention is to stepwise or continuously apply predetermined lower concentrations of cryoprotectant to the biological cells of a particular type or species to remove cryoprotectant from the cells.

A third aspect of this invention are cells that have had cryoprotectant removed in accordance with the methods described in this invention.

A fourth aspect of this invention is a method to predict appropriate protocols to add cryoprotectant to biological cells based on the cells' lower volume limit, the cell membrane's cryoprotectant permeability coefficient, and the cell membrane's water permeability coefficient.

A fifth aspect of this invention is to stepwise or continuously apply predetermined higher concentrations of cryoprotectant to the cells of a particular type or species to add cryoprotectant to the cells.

A sixth aspect of this invention are biological cells containing cryoprotectant, where the cryoprotectant was added to the cells in accordance with the methods described in this specification.

A seventh aspect of this invention is a membrane particularly suited to add or remove cryoprotectant to or from a biological cell at a predetermined rate where the cell's volumetric limits are not exceeded.

An eighth aspect of this invention is a device to observe a biological cell's swelling or shrinking under anisosmotic conditions over time.

A ninth aspect of this invention is a device to add a cryoprotective agent to or to remove a cryoprotective agent from a biological sample that uses a membrane particularly suited to do so for a particular cell type without exceeding a predetermined cell volume of that cell type.

Furthermore, this invention has the following advantages over the empirical approach of the prior art:

(1) the method is usable for other cryoprotectants besides the commonly used glycerol, dimethyl sulfoxide, or ethylene glycol.

(2) the method is usable to predict protocols for differing concentrations of cryoprotectants and at different temperatures.

(3) the use of modeling is faster and cheaper than empirical methods (basically trial and error). And, much information can be determined before actual use, like: (a) minimum time interval between cryoprotectant addition/removal steps and/or exact rates to safely add or remove CPA (b) maximum amount of cryoprotectant or diluent used for each step, and (c) the least number of steps or minimum time required to prevent osmotic injury. This information is otherwise not readily available especially if one changes cell type or species, type of cryoprotectant, cryoprotectant concentration, or even temperature of the cryoprotectant's use.

Within this application, the term "predetermined concentration" refers to a concentration that has been calculated not to exceed or not to substantially exceed the biological cells' upper volume limit (CPA removal) or lower volume limit (CPA addition) using the permeability coefficients of water and cryoprotectant through the cell's membrane.

Within this application, the term "contacting" refers to the physical contact that allows cryoprotectant and water to pass through a cells' membrane.

Within this application, the term "volumetric excursion" refers to the cells' volume substantially shrinking or substantially swelling beyond limits that have been predetermined to cause a predetermined percentage of cells to be injured.

BRIEF DESCRIPTION OF THE DRAWINGS

In the accompanying drawings, forming a part of this specification.

DESCRIPTION OF THE PREFERRED EMBODIMENTS

Figure 1:
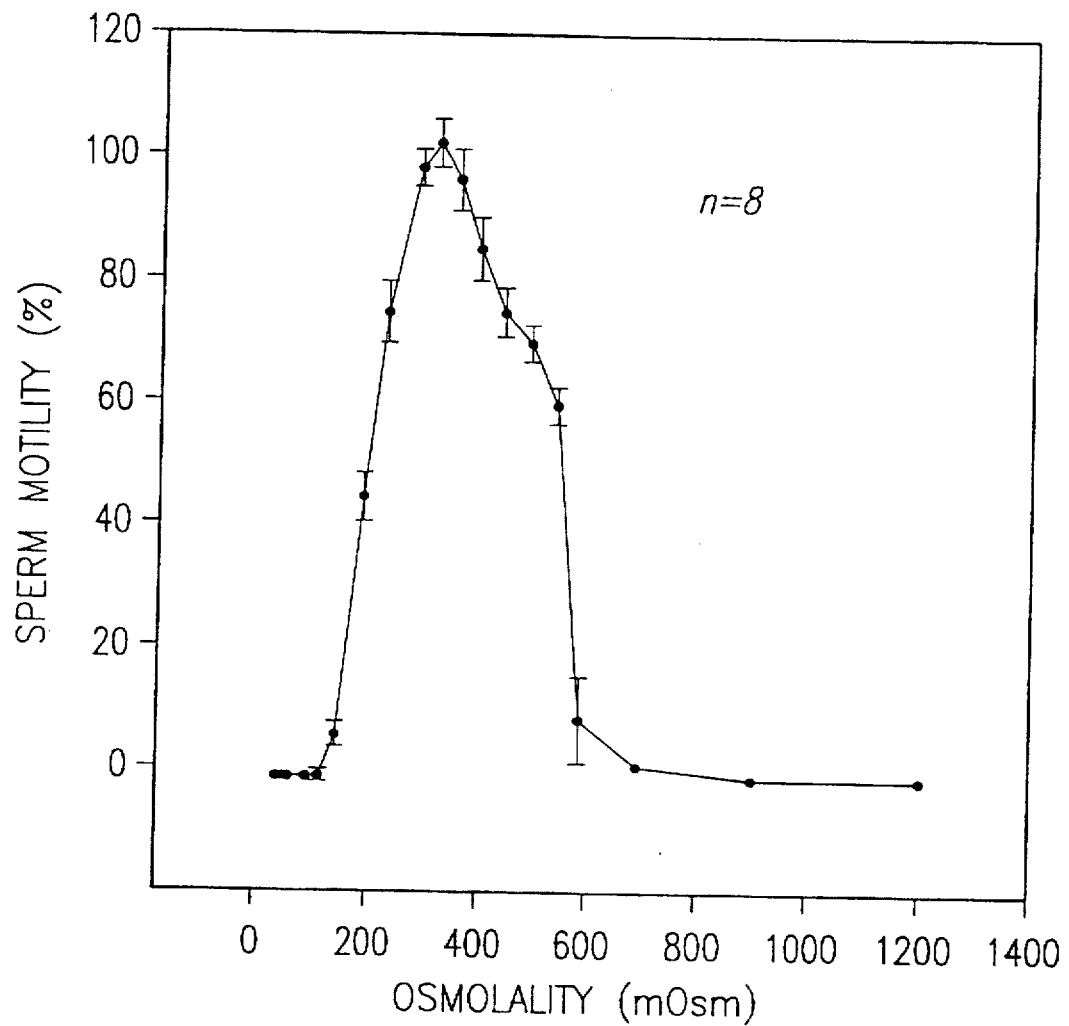
FIGS. 1 to 4 are graphical portrayals of examples of injury to sperm cells as a function of osmolality.

Specific language is used to describe several embodiments of this invention to promote an understanding of the invention and its principles. It must be understood that no limitation of the scope of this invention is intended by using this specific language. Any alteration and further modification of the described methods or devices, and any application of the principles of this invention are also intended that normally occur to one skilled in this art.

Osmotic stress is known to cause injury to biological cells such as sperm, blood, or pancreatic islet cells. Cells experience this stress during the passage of cryoprotective agent (CPA) across the cell membrane, both into or out of the cells. The stress is typically caused by cells shrinking or swelling beyond or below their volumetric limit during the passage of CPA through the cell membrane. The present methods and devices optimize CPA addition or CPA removal for a predetermined cell type by reducing this stress. For presentation purposes, this invention is described in several aspects. The first aspect concerns finding upper and lower volumetric limits of a particular biological cell type. The second aspect concerns finding the water and cryoprotectant permeability coefficients of the particular cell type. The third aspect concerns predicting conditions to transport water and CPA across the cell membrane based on these volumetric limits and permeability coefficients. The fourth is a membrane that effectively regulates the transport conditions of water and CPA into or out of the cell based upon these predictions. Finally, the fifth are several devices that incorporate the use of this membrane.

A first aspect of this invention concerns evaluating a particular cell type for its volumetric limits or its osmotic tolerance. Osmotic tolerance refers to a cellos ability to withstand shrinking or swelling without injury. In particular, this evaluation determines a cell's volumetric limits to swelling and shrinking before a user-defined percentage of the cells lose their viability, for example, lose their motility, lose their ability to be fertilized, or simply lyse. Typical user-defined percentages of viability loss may be as high as 50%, or as low as 20%, 10%, 5%, or even less than 1%.

A preferred procedure to determine osmotic tolerance is to first expose the cells to various anisosmotic solutions, noting the degree of cell injury that occurs upon exposure to a particular osmotic pressure for a particular period of time. Typical anisosmotic solutions might range from 40 to 1200 mOsm (milliosmols); however, the exact anisosmotic solutions may vary with the type and species of cells and any user preferences. Typical anisosmotic exposure times might range from as little as 5 seconds to as long as 30 minutes. After exposure, the cell sample is evaluated for the degree that cells in the sample lose their viability, for example, a measurement of the loss of a specific ability or simply the degree of lysing that occurs. Both the exposure step and the evaluation step are repeated over a range of anisosmotic solutions so as to experimentally correlate the degree of cell injury with osmotic pressure and time of exposure.

One preferred procedure to assess cell viability utilizes dual flourescent staining and flow cytometric analysis as disclosed by Garner in *Assessment of Spermatozoal Function Using Dual Fluorescent Staining and Flow Cytometric Analysis*, Biol. Reprod. 34, 127–138, 1986, which is hereby incorporated into this specification by reference. Propidium iodide (PI) is a bright red, nucleic acid-specific fluorophore available from the Sigma Chemical Co. PI permeates poorly into sperm cells with intact plasma membranes, however, it readily diffuses into sperm having damaged membranes and stains the DNA red. 6-Carboxyfluoroscein diacetate (CFDA) is a membrane-permeable compound which is also available from the Sigma Chemical Co. CFDA penetrates into the sperm and is hydrolyzed by intracellular esterase to 6-carboxy fluoroscein (CF). CF is a bright green, membrane-impermeable fluorophore. Thus, when CFDA is added into the sperm suspension, membrane-intact spermatozoa fluoresce bright green. Membrane integrity is then tested by exposing a sperm sample to a solution containing both PI and CFDA and performing flow cytometric analysis upon the sperm sample after contact and basing the analysis upon the amount and/or location of the color present. Similar stains and testing procedures are quite common for other cell types and are well within the skill of this art to obtain and use.

Another method to determine cell viability (here, the loss of sperm cell motility) utilizes computer assisted semen analysis (CASA) using CELLSOFT™ (for example version 3.2/C available from CRYOResorces™, LTD). CASA is a widely recognized method to determine sperm cell motility, having been used for many years and is well within the skill of this art to use. For example, see A. Jequier and J. Crich, in *Semen Analysis: A Practical Guide*, Blackwell Scientific Publication, Boston, 1986, the disclosure of which is hereby incorporated into this specification by reference.

Next, once the user-defined upper and lower osmotic limits are determined, the Boyle van't Hoff relationship is utilized to find the corresponding upper and lower volume limits of the cell. This equation is a simple linear relationship:

$$V_w = V_i(M_i/M) + V_b$$

where $V_w$ is the volume of a cell at osmolality M, $V_i$ is the volume of an osmotically active cell at the isotonic osmolality, $M_i$; and $V_b$ is the volume of an osmotically inactive cell. This equation is discussed in *Osmotic Behavior of Human Spermatozoa Studied by EPR*, by Du, Kleinhans, Mazur, and Critser, in Cryo-Letters, 14, 285–294 (1993), the disclosure of which is hereby incorporated into this specification by reference.

The volume of an osmotically inactive cell, $V_b$, is that volume of a cell that includes both cell solids and osmotically inactive water. This parameter can be somewhat temperature dependent, however, this fact does not frustrate the present invention. $V_b$ is found by experimentally recording the volume of a cell for several known osmolalities. For nearly spherical cells, this is accomplished by simply measuring the cells new diameter measured at a known osmotic pressure and simply calculating the volume of the round cell. $V_b$ is then simply the y-intercept of a plot of known cell volumes, normalized to the cell's isotonic volume, versus each volume's corresponding normalized osmotic pressure. This calculation is well within the skill in the art to perform.

Two preferred methods exist for determining $V_b$ for non-spherical cells like blood and semen, as well as for monitoring their kinetic volume change, discussed later in this specification. The first of these is electron paramagnetic resonance (EPR). In EPR, the water volume of a non-spherical cell is determined my measuring the intracellular signal strength of the spin label, tempone, to which the membrane is permeable. Any extracellular signal of tempone is eliminated by adding a line-broadening agent, chromium oxylate, which is cell membrane impermeable.

Another preferred method for determining $V_b$ for non-spherical cells is the use of an electronic particle counter such as a Coulter Counter from Coulter Electronics, Inc., Hialeah, Fla., United States. The Coulter Counter is interfaced with a microcomputer, for example, by a CSA-1S interface (The Great Canadian Computer Company, Alberta, Canada). The system can be calibrated by simply using styrene beads of known volume such as those sold by Duke Scientific Corporation, Palo Alto, Calif. Two data acquisition modes are generally supported in this arrangement. One is a histogram (volume distribution) of particle count versus volume. A second is the average cell volume versus time, which is generated by computing the average cell volume over short (e.g. 220 msec) time intervals. The former is used to determine values to find $V_b$, the later offers data for the kinetic volume analysis discussed later in this specification.

A second aspect of this invention is to determine the permeability coefficients of a given cell type, namely, the water permeability coefficient of the cell membrane, $L_p$; the cryoprotectant permeability coefficient of the cell membrane, $P_{CPA}$; and the reflection coefficient, σ. These cell parameters are found with the aid of 4 first-order, non-linear equations and are discussed in *Thermodynamic Analysis of the Permeability of Biological Membranes to Non-Electrolytes*, by Kedem and Katchalsky, in Biochimica et Biophysica ACTA, Vol. 27 (1958), the disclosure of which is hereby incorporated by reference into this specification.

The first two equations respectively describe total membrane volume flux ($J_v$) and transmembrane permeable solute flux ($J_{CPA}$). Assuming the solution consists of a single permeable solute (here, CPA) and other impermeable solutes (i.e. salt), the mathematical equations are:

$$J_v = 1/A_c \, dV(t)/dt \qquad \text{Equation 1}$$
$$= -L_p\{(C^e_{salt} - C^i_{salt}) + \sigma(C^e_{CPA} - C^i_{CPA})\}$$

and, $$J_{CPA} = 1/A_c \, dN_{CPA}/dt \qquad \text{Equation 2}$$
$$= \overline{C}_{CPA}(1 - \sigma)J_v + P_{CPA}(C^e_{CPA} - C^i_{CPA})RT$$

where $J_v$=total volume flux, V=cell volume, t=time, N=mole number of the solute, $A_c$=cell surface area, $L_p$=water permeability coefficient of the cell membrane, C=concentration of solute, $J_{CPA}$=CPA flux across the cell membrane, superscript e=extracellular, superscript i=intracellular, $\overline{C}_{CPA}$=average CPA concentration of extracellular and intracellular concentrations. Furthermore, R=gas constant, T=absolute temperature, $P_{CPA}$=CPA permeability coefficient of the cell membrane, and σ=the reflection coefficient of the particular CPA. The reflection coefficient is generally specific to a particular cryoprotectant and represents the opposing actions of water and cryoprotectant moving in opposite directions through the cell membrane. Typically it is assumed to be 1. For example, using glycerol as the CPA, a value of 0.7 to 1 has only insignificant effect on the predictions found using this model. However, it must be remembered that its exact value is dependent on the cryoprotectant utilized and is a point where the user may fine tune the model for their particular use. Using the devices and methods discussed further in this patent, a more exact value can be determined.

The second two equations are mathematical models for intracellular concentrations of impermeable solute (salt) and permeable solute (CPA), and are:

$$C_{salt}^i(t) = C_{salt}^{*,0}\{(V(0) - V_b - \bar{V}_{CPA}N_{CPA}^{i,0})/(V(t) - V_b - \bar{V}_{CPA}N_{CPA}^i(t))\} \quad \text{Equation 3}$$

$$C_{CPA}^i(t) = [N_{CPA}^i(t)]/[V(t) - V_b - \bar{V}_{CPA}N_{CPA}^i(t)] \quad \text{Equation 4}$$

where $V_b$=osmotically-inactive cell volume, $\bar{V}_{CPA}$=partial mole volume of CPA, N=mole number, and 0=initial condition (t=0). Initial conditions for V(0) $C_{salt}^i(0)$, $C_{CPA}^i(0)$ $N_{CPA}^i(0)$ are known based upon the actual conditions present. When using these models in computer simulation, it can be assumed that (a) extracellular concentrations of permeating and non-permeating agents are constant, and that (b) the mixture of solutions during the CPA addition and removal are instantaneous.

The water permeability coefficient, $L_p$, the cryoprotectant permeability coefficient, $P_{CPA}$, and the reflection coefficient of the particular CPA, $\sigma$, are found using equations 1 to 4 and data of a particular cell's kinetic volume change over time for a given cryoprotectant concentration and temperature. Using this data, the user simply solves equations 1 to 4 for $L_p$, $P_{CPA}$, and $\sigma$. For round cells this can be accomplished by simply measuring a cell's volume change over time upon exposure to a CPA of known concentration and temperature as the perfusion of the CPA into or out from the cell occurs. The investigation proceeds by directly monitoring the dimensional change of the cell before, during, and after the perfusion by video camera until an osmotic equilibrium is reached. The videotaped images are then processed using a digital image analyzer such as The Dynamic Morphology System, sold by Motion Analysis Corp. of Santa Rosa Calif. to determine the time dependence of the change in the radius of the cell during the perfusion process. The radius is related to volume by assuming spherical geometry. This procedure is discussed in the following articles the disclosure of which is hereby incorporated by reference: McGrath et al., *Coupled Transport Across the Murine Oocyte Plasma Membrane: Water and Cryoprotective Agents*, HTD-Vol. 206-2, Topics in Heat Transfer—Volume 2 ASME 1992; Bernard et al. *A Preliminary Study Comparing Murine and Human Ova*, 1988 Cryobiology 25, pp. 495–501; Hunter et al., *Measurements of the Membrane Water Permeability and it's Temperature Dependence (Activation Energy) in Human Fresh and Failed-to-Fertilize Oocytes and Mouse Oocyte*, 1992a Cryobiology 29, pp. 240–249; McGrath et al., *Determination of the Temperature-dependence of Biomembrane Passive Transport Using a Microdiffusion Chamber*, Bioheat Transfer—Applications in Hyperthermia, Emerging Horizons in Instrumentation and Modeling, ASME Press, HTD Vol 126, BED Vol 12, pp. 137–142; and McGrath et al., *On the Use of MicroDiffusion Chamber Methods to Determine The Coupled Transport of Water and Cryoprotective Agents Across Biological Membranes*, Macroscopic and Microscopic Heat and Mass Transfer in Biomedical Engineering, Elsevier Press, pp. 271–296. EPR and an electron particle counter, discussed earlier, are preferably used for non-spherical cells. As example values found using these procedures, Table 1 identifies relevant values for human sperm.

TABLE 1

| Known characteristics of human spermatozoa | |
|---|---|
| Surface area (A) | 120 um$^2$ |
| Volume (V) | 34 um$^3$ |
| Osmotically inactive volume (V$_b$) | 16.6 um$^3$ |

TABLE 1-continued

| Known characteristics of human spermatozoa | |
|---|---|
| Water permeability coefficient (Lp) (22° C.) | 2.16 um/minutes/atm |
| Glycerol permeability coefficient (P$_{CPA}$) (22° C.) | 1.1 × 10$^{-3}$ cm/minutes |

The chamber in which a spherical cell is analyzed and in which the foregoing kinetic data is collected is of critical concern. It is important that the chamber allow the cell to freely swell and shrink upon exposure to a particular CPA of known concentration and temperature. Two such chambers are shown in FIGS. 1A and 2A. Referring first to FIG. 1A, a perfusion chamber 20 is generally identified in cross-section. The chamber has a glass plate 21 and 22 on each of its sides so that one may view inside the chamber through the lens 23 of a stereoscope or microscope. In the middle of the device is membrane 24. A biological cell 25 under consideration is placed upon this membrane in isotonic solution. The membrane has pores that are significantly smaller than the outside dimensions of the cell so that the cell will not wash away as isotonic fluid or CPA flows around it. Support plates 26 and 27 reside on each side of the membrane, each having and aperture 28 to allow fluid access to cell sample 25 residing upon membrane 24. At the start, an isotonic fluid is flowed past cell 25 through inlet 29 and exits through outlet 30. The temperature of the system is monitored with thermocouple 31. After the cell is equilibrated in the isotonic fluid, CPA of known concentration and temperature is introduced at 29 and allowed to exit at 30. The sample is continually monitored for its change in size in respect to time with a video camera. The run is complete when the cell has reequilibrated itself to the new osmotic environment resulting from the introduction of the CPA. The images taken from the video tape are then digitally analyzed as previously presented.

Referring next to FIG. 2A, another version of the perfusion chamber is shown. Like numbers are employed to identify structures similar to those in FIG. 1A. This embodiment has a lid 37 that holds down the outer edge of glass plate 21 and leaves glass plate 21 accessible from above the device. A base mount 38 similarly holds glass plate 22 into position and allows access to glass plate 22 from below the device. Both the base mount 38 and lid 37 are mounted onto body 39. Body 39 has a chamber 40. Inlet 29 opens into chamber 40 and outlets 41, 42, 43, and 50 exit from chamber 40. A center mount 45 resides in chamber 40, between glass plates 21 and 22. The center mount has a passage 46 that opens into outlet 43. Atop the center mount is membrane 24, then atop the membrane is spacer 47. Spacer 47 has a bore 48 in communication with passage 46, separated only by membrane 24. Finally, it is important that a gap 49 exist between spacer 47 and plate 21. This gap is preferably of a width to provide laminar flow around the cell sample as a CPA enters bore 48 during use. Typically this would be in the range of 0.5 to 0.1 millimeters or even less.

Figure 3:
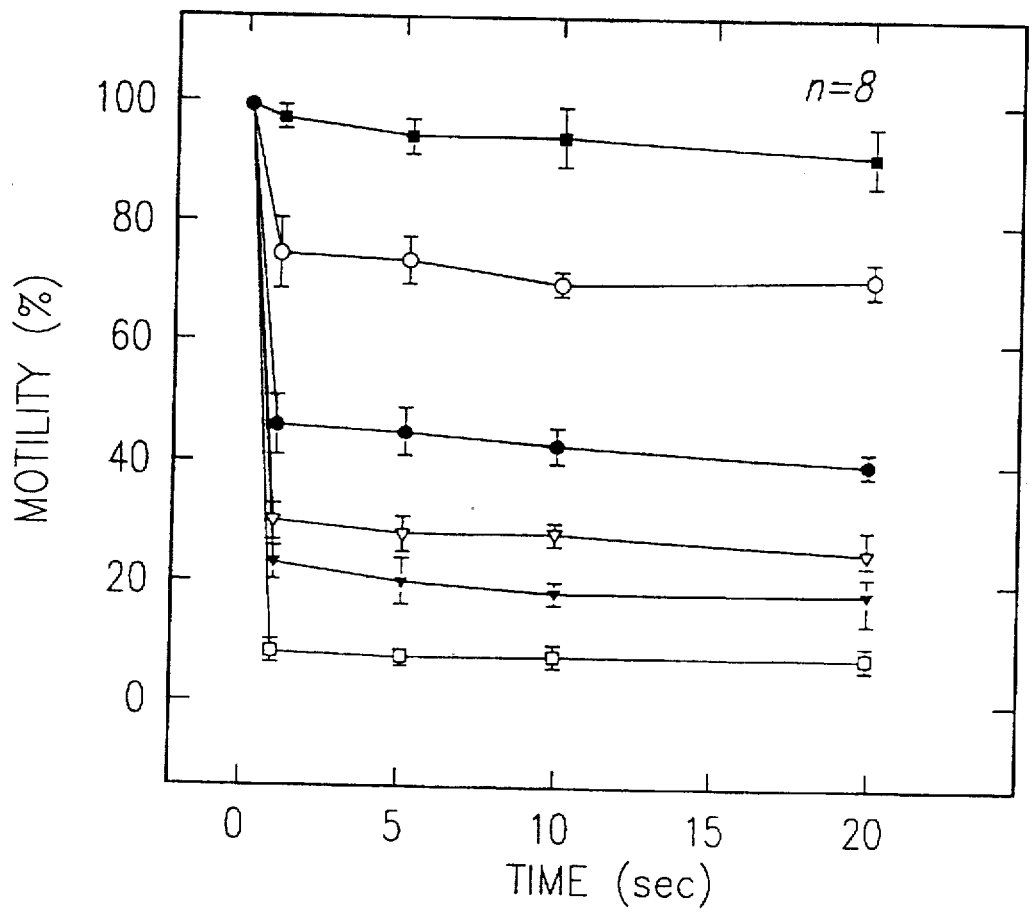
Figure 3A:
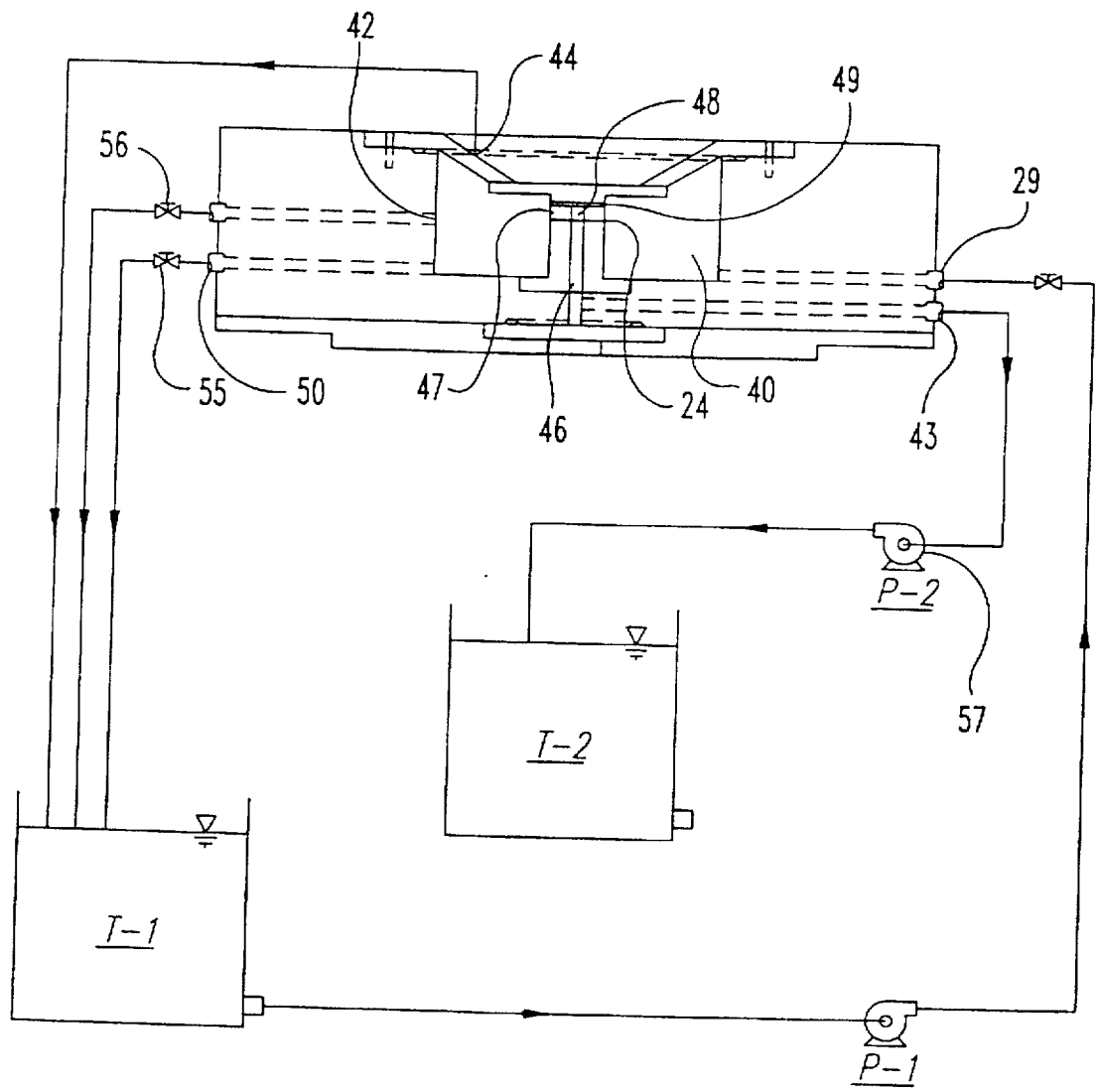
FIG. 3A is flow chart showing a preferred use of a perfusion chamber.

The operation of the second device is shown in FIG. 3A. A cell sample is placed in isotonic solution within bore 48, and upon membrane 24. Valve 55 is closed and valve 56 is opened. CPA of a known concentration enters the device at inlet 29 and flows into chamber 40. Camber 40 partially fills up to the level of outlet 42, but not above membrane 24. The CPA is continually flowed through the device past inlet 29 and outlet 42 until a temperature equilibrium is maintained. At that point, valve 56 is closed, allowing CPA to exit at outlet 44, and pump 57 is started. Pump 57 pulls the isotonic solution from bore 48, down passage 46, and through outlet 43 to replace the isotonic solution around the cell sample with CPA that enters through gap 49. In this fashion, a controlled exposure of the cell to the CPA can be observed and video data of the cell's volume change taken. The video is analyzed digitally as discussed immediately above. Valve 55 can then be reopened to drain chamber 40 through outlet 50.

Although, the above devices and equations only allow $L_P$, $P_{CPA}$ and $\sigma$ to be determined for a specific temperature, others can be calculated. For example, using the equation:

$$L_p(T)=L_p(T_0)\exp\,[-E_a/R(1/T-1/T_0)]$$

the permeability coefficient can be calculated at other temperatures. $T_0$ refers to some reference temperature and R is the the gas constant. The activation energy, $E_a$, is simply found by linear analysis of the slope of known data points ($L_p$ and T). Using other data points ($P_{CPA}$ and T, or $\sigma$ and T) other activation energies are similarly found to calculate these constants at a new temperature, as well.

Once the volume limits and permeability constants are known, the kinetics and effects of various schemes of CPA addition or removal to a solution of biological cells are evaluated using previously identified equations 1 to 4. Once a particular concentration of cryoprotectant is chosen, the equations (1–4) are utilized in iterative fashion to determine whether the cell's upper or lower volume limit has been exceeded or significantly exceeded. The placement of these equations into computer code to perform this calculation is within the skill of this art.

Examples of the physical values for human sperm needed are shown in Table 1. Similar values for other species of sperm are within the skill in the art to obtain. For example, the permeability coefficient of the cryoprotective agent can be determined using procedures as disclosed in *Glycerol Permeability of human Spermatozoa and its Activation Energy*, by Gao, Mazur, Kleinhans, Watson, Noiles, and Critser, Cryobiology 29, 657–667, the disclosure of which is hereby incorporated by reference into this specification; or, the permeability coefficient of water can be determined using procedures as disclosed in *Determination of Water Permeability Coefficient for Human Spermatozoa and its Activation Energy*, by Noiles, Mazur, Watson, Kleinhans, and Critser; Biology of Reproduction 48, 99–109 (1993) the disclosure of which is also hereby incorporated by reference into this specification.

In review, the user of this invention first determines the concentration of cryoprotectant desired to be added or removed from a cell suspension. Afterward, equations 1 to 4 are utilized in iterative fashion, typically with the aid of a computer, to determine whether the addition or removal of this concentration of cryoprotectant causes the biological cells to shrink or swell beyond their predetermined lower or upper volumetric limit. Examples of schemes to add cryoprotectant to cell suspensions of given initial concentration include: (1) the multi-step addition or removal of CPA in constant volumes, (2) the multi-step addition or removal of CPA in constant molarity changes, or (3) the multi-step addition or removal of CPA in the presence of a non-permeating solute as an osmotic buffer.

Fixed-Volume-Step (FVS) Addition of CPA

The addition of CPA medium to a cell suspension, in fixed volumes, is calculated with the following equation:

$$V_i=[(M_fV_o)(M_o-M_f)]1/n \qquad \text{Equation 5}$$

where $M_f$=final CPA concentration in a cell suspension (molarity), $M_o$=CPA concentration in original CPA medium (molarity), n=total number of stages, i=ith step addition (In this specification ith step or kth step refers to one of the total steps undertaken, for example ith (kth) could be the 4th step of 8 total steps), $V_o$=original volume of isotonic cell suspension, and $V_i$=volume of CPA medium added into the cell suspension at each step of a multi-step addition.

Fixed-Molarity-Step (FMS) Addition

The addition of CPA medium to a cell suspension, in fixed molarity increases, is calculated with the following equation:

$$V_i=(M_fV_onM_o)/[(nM_o-iM_f)(nM_o-(i-1)] \text{ for } i=1 \text{ to } n \qquad \text{Equation 6}$$

or $$V_i=[1/(\lambda n-i)]V_{i-1}^* \qquad \text{Equation 7}$$

where $$V_{i-1}^*=V_o+\Sigma V_k \text{ for } k=1 \text{ to } i-1 \qquad \text{Equation 8}$$

and where $$\lambda=M_o/M_f \qquad \text{Equation 9}$$

and $$\Delta M=M_f/n \qquad \text{Equation 10}$$

where $M_f$=final CPA concentration in cell suspension (molarity), $M_o$=CPA concentration in original CPA medium (molarity), n=total number of steps, i=ith step addition, $V_o$=original volume of isotonic cell suspension (ml), $\Delta M$=increment of CPA molarity in cell suspension after each step of CPA addition, $V_{i-1}^*$=the total volume of cell suspension before the ith step addition, $V_i$=volume of CPA medium added into the cell suspension at the ith step.

Fixed-Volume-Step (FVS) Removal

Given the initial volume of the cell suspension ($V_o$) and the initial concentration of the CPA ($M_o$), the total volume of isotonic solution required to dilute CPA concentration from $M_o$ to $M_s$ is calculated by the following:

$$V=V_o\{(M_o/M_s)-1)\} \qquad \text{Equation 11}$$

Using the FVS scheme, the volume of isotonic solution added into cell suspension at the ith step during the first n−1 steps (n steps in total) is calculated as follows:

$$V_i=V/(n-1)=[V_o/(n-1)][(M_o/M_s)-1] \qquad \text{Equation 12}$$

where $M_s$=CPA concentration in cell suspension (molarity) after n−1 step dilutions, $M_o$=CPA concentration in initial cell suspension (Polarity), n=total number of steps, i=the ith step addition, $V_o$=original volume of cell suspension (ml) and $V_i$=volume of isotonic solution added into the cell suspension at the ith step. After n−1 steps of adding isotonic solution into the cell suspension, the diluted cell suspension is centrifuged, for example, at 400 g for 5–7 minutes., and then the cell pellet is resuspended in isotonic solution to make the last (nth) step dilution.

Fixed-Molarity-Step (FMS) Dilution

In this scheme the CPA concentration in the cell suspension is stepwise diluted by adding isotonic solution and decreasing the molarity of the CPA in fixed steps. The following equation is used to calculate the volume of isotonic solution added into the cell suspension at the ith step during the first n−1 steps (n steps in total)

$$\Delta M=M_o/n \qquad \text{Equation 13}$$

$$V_i=[1/(n-1)]V_{i-1}^*, i=1 \text{ to } n-1 \qquad \text{Equation 14}$$

$$V_{i-1}^*=V_o+\Sigma V_k, k=1 \text{ to } i-1 \qquad \text{Equation 15}$$

where $\Delta m$=decrement of CPA molarity in the cells after each step addition of the isotonic solution, $M_o$=CPA concentration in initial cell suspension (molarity), n=total number of steps, i=ith step addition, $V_o$=original volume of cell suspension, $V_{i-1}^*$=the total volume of cell suspension before the ith step addition, and $V_i$=volume of isotonic solution added into cell suspension at ith step. After n−1 steps of the addition, the CPA concentration in the cells is diluted to $\Delta M = M_o/n$. Then the cells will be transferred to isotonic conditions, which makes the last (the nth) step removal of CPA.

EXAMPLES

Example 1A

Finding Upper and Lower Volumetric Limits with EPR

Materials: Tempone (4-oxo-2,2,6,6-tetramethylpiperidine-1-oxyl) was purchased from Molecular Probes, Eugene, Oreg. Chromium oxalate ($K_3|Cr(C_2)_4)_3|\cdot 3H_2P$; CrOx) was synthesized according to the procedure of Bailar and Jones, Inorg. Synthesis 1, 35–38 (1939). Sodium chloride and trypan blue were obtained from Sigma Chemical Company. Phosphate buffered saline (PBS) was used for the human red blood cell (RBC) study and modified Tyrode's medium, TALP (see Barrister, Leibfried, and Lieberman, Biol. Reprod. 28, 235–247 (1983)), utilizing 4 mg/ml of bovine serum albumin was used for the human spermatozoa study.

Human RBC Preparation: Human blood was obtained by venipuncture from three healthy donors into 10 cc vacutainer tubes with acid citrate dextrose (SCD) anticoagulant. Cells were washed three times by centrifugation at 1000×g for five minutes each in PBS (pH=7.4) prior to use.

Human Sperm Preparation: Human sperm was obtained by masturbation from ten healthy donors after at least two days sexual abstinence. Samples were allowed to liquefy in an incubator (5% $CO_2$/95: air, 37° C., high humidity) for approximately 30 minutes, and then a computer assisted semen analysis (CASA) was performed (CellSoft, Cryo Resources, Ltd, New York) to determine cell concentration and percent motility.

A swim-up procedure was performed by layering 500 µl of TALP over 250 µl of semen, incubating for about 1.5 hours in the incubator and carefully aspirating 400 µl of the supernatant. Because of the requirement for a large number of cells in the EPR experiments, samples from two donors were pooled for each osmotic experiment. The semen samples were analyzed, a swim-up procedure performed separately on each sample, and the swim-up supernatants mixed prior to the experiment. The original (pre-swim-up) semen samples used in this study had motilities greater than 40% and after swim-up preparation, the motilities exceeded 90%. The swim-up samples were maintained in an incubator (5% $CO_2$/95% air, 37° C., high humidity) and used within 5 hours.

EPR sample preparation: Two µl of 50 nM tempone, 10 m µl of 250 mM CrOx, 28 µl of sodium chloride solution (83, 153, 345, 694, 1217, or 2270 mOsm), and 10 µl packed sperm cells in TALP (centrifuged at 400×g for 10 minutes) were combined in a 5 ml sterile culture tube. The combined solution had a total volume of 50 µl containing final concentrations of 2 mM tempone, 50 mM CrOx, and a total osmotic concentration of 250, 290, 400, 600, 900, or 1500 mOsm. The contents were mixed manually by tapping the tube. Ten µl of each sample was transferred to another tube for trypan blue staining (10 µl sample and 10 µl 2@ trypan blue in isotonic saline, incubated for 10 min.) and cell counting of membrane intact cells on a standard hemocytometer under a light microscope which yields the sample cell concentration, $C_c$. The remaining sample was drawn by capillary action into a 50 µl disposable micropipet (Clay Adams #4622, Parsippany, N.J.) and sealed with Crioseal (Monoject Scientific, St. Louis, Mo.) for the EPR measurement. All the final osmotic concentrations were determined by linear addition of the individual osmolalities of the sodium chloride and CrOx (non-permeating solute). The osmolality of tempone was not included in the final concentration because it is a cell membrane permeable solute and has a very low concentration. The final strength of each solution was checked on a freezing point depression osmometer (Advanced DigiMatic Osmometer, Model 3D2) yielding agreement within 3%. The high concentration of tempone, 2 mM, was chosen to optimize signal strength and leads to some spin-spin line broadening.

The protocol used for the human RBC study was the same as for the human sperm study except for the use of PBS in place of TALP and the omission of trypan blue staining in the hemocytometer samples.

A reference sample was prepared using 2 µl of 50 mM tempone and 48 µl TALP (or 48 µl PBS) for the human sperm measurements (human RDC measurements). Since the extracellular spin label signal could not be broadened away completely, a background sample for each osmotic concentration was prepared using the same protocols as stated earlier except for omitting the cells and using pure buffer in place of the cell pellet.

EPR data acquisition and analysis: EPR measurements were made at 20°±0.5° C. on a Varian X-Band E109 spectrometer with a rectangular cavity and an HP9825 data system with custom software for biological spin label work. The parameters used in the experiments were (a) power 20 mW; (b) magnetic field 3275 gauss; (c) field sweep 25 gauss; (d) modulation amplitude 0.5 gauss; (e) amplifier time constant 0.128 seconds; and (f) variable rate sweep yielding a total sweep time of 350 sec. For each background spectrum, the time constant was increased to 0.25 seconds and the total sweep time increased to 700 seconds. To improve the signal to noise ratio, a variable rate sweep was used in which additional time (9 times) was spent in the peak regions of the spectrum, with digital signal averaging (9). These spectra were then analyzed using a least squares, third order polynomial fitting routine to pick out each positive and negative peak. This procedure yielded good immunity from noise.

EPR cell volume measurements were performed. The principle is that the water volume of cells is proportional to the intensity of the intracellular spin label signal. Tempone labels all aqueous compartments of the sample, both intra- and extracellular, and a cell membrane impermeable broadening agent, CrOx, is used to broaden away the extracellular signal. The remaining extracellular signal of tempone can be eliminated by digital subtraction of the background control spectra from the sample spectra. The fractional volume, $F_v$, is defined as that fraction of the total sample volume which is attributable to intracellular water. It is found by taking the ratio of the intensities, $I = W^2 h$, of the intracellular signal to a reference standard with the same spin label concentration:

$$F_v = I(\text{intracellular})/I(\text{reference})$$

where W and h are the peak to peak line width and height of the midfield line, respectively. Then the average water volume per cell, $V_w$, is obtained by dividing the fractional volume by the concentration of cells with intact membranes, $C_c$.

$$V_w = F_v/C_c$$

For instance, a fractional volume, $F_v$, of $2.0 \times 10^{-3}$ and a cell concentration, $C_c$, of $1.5 \times 10^8$ cells/ml yields a cell volume, $C_v$, of $1.3 \times 10^{-11}$ ml which equals 13 μn³.

Example 1B

Finding Upper and Lower Volumetric Limits

The human semen used in this example was obtained by masturbation from healthy donors after at least two days of sexual abstinence. The samples were allowed to liquefy in an incubator for 1 hour, at 37° C., in high humidity, and in 5% $CO_2$ and 95% air. A swim-up procedure was performed to separate motile sperm from immotile sperm. The motile sperm suspensions were centrifuged at 400×g for 7 minutes and then were resuspended in isotonic TL-Hepes medium, that is, HEPES-buffered TALP medium (286–290 mOsm) supplemented with Pyruvate (0.01 mg/ml) and BSA (4 mg/ml), at a cell concentration of $1 \times 10^9$ sperm/mil.

Sperm motility was measured by computer assisted semen analysis (CASA) using CELLSOFT™, version 3.2/C. CASA was performed before, during, and after the anisosmotic exposures of the sperm samples. All experiments were conducted at 22° C.

Plasma membrane integrity was analyzed by placing five μl of CFDA (suspended in 0.25 mg/ml of DMSO) and 5 μl of PI (suspended in 1 mg/ml $H_2O$) solutions into 0.5 ml of a particular sperm suspension. The cells with CFDA staining and without PI staining were considered as intact cells. An analytical determination of the percentage of intact sperm remaining in each sample was then made. A total of $1 \times 10^5$ spermatozoa per treatment were analyzed using a FACSTAR PLUS™ flow cytometer.

The FACSTAR PLUS™ flow cytometer settings were:
(1) Gates were set using forward and 90° light scatter signals at acquisition to exclude debris and aggregates.
(2) Instrument alignment was performed daily with fluorescent microbead standards to standardize sensitivity and setup.
(3) Photomultiplier settings were adjusted for spectral overlap with individually stained cells.
(4) Excitation was at 488 nm from a 4 Watt Argon laser operating at 200 mWatts. Fluorescein emission intensity was measured using a 530/30 bandpass filter, and PI intensity using a 630/22 bandpass filter.

Anisosmotic solutions ranging from 40 to 1200 mOsm were prepared using only non-permeating solutes and water. Hyposmotic solutions were made by diluting TL-HEPES medium with reagent grade water. Hyperosmotic solutions were prepared by adding sucrose or NaCl to the TL-HEPES medium. (Sucrose, NaCl, and the solutes in the TL-HEPES medium were considered to be membrane-impermeable compounds.)

Ten μl of the isotonic cell suspension (286–290 mOsm, $1 \times 10^9$ sperm/ml) were mixed with 150 μl of each anisosmotic solution. After CASA, and a time period from 5 seconds up to 30 minutes, the sperm in each anisosmotic solution were ultimately returned to isotonic condition by adding 150 μl of isotonic TL-HEPES medium to 10 μl of each anisosmotic sperm suspension. (The percentage of sperm which maintained motility or plasma membrane integrity after each treatment was normalized to that of sperm in untreated control samples for the following discussion.)

Figure 1A:
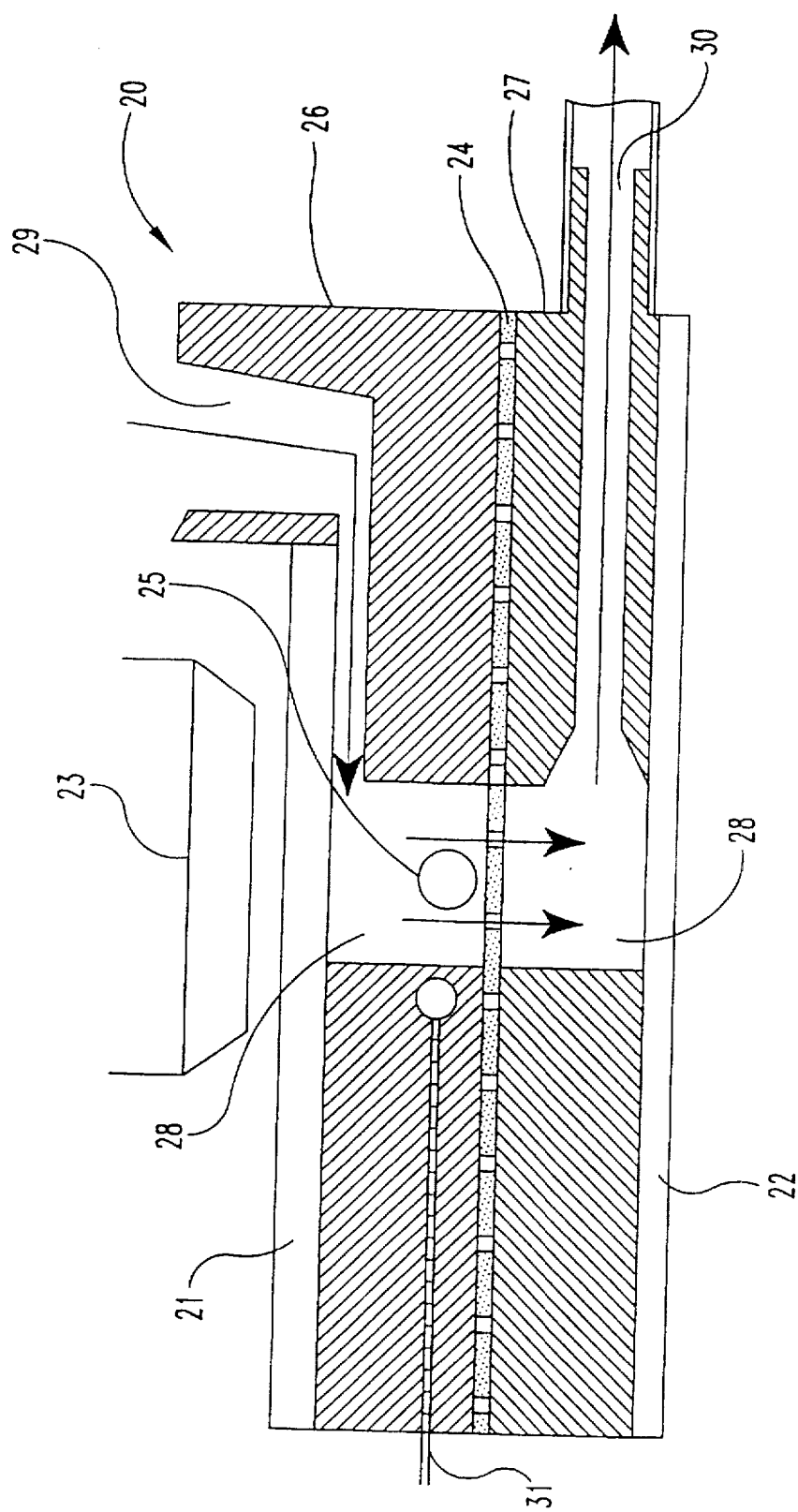
FIGS. 1A and 2A are cross-sections of preferred embodiments of a perfusion chamber to observe the kinetic volume change of a biological cell.

The normalized percentage of motile sperm in anisosmotic solutions (containing nonpermeable solutes only) ranging from 40 to 1200 mOsm is shown in FIG. 1. It was observed under microscopy (a) that a part of sperm lost their motility immediately after being exposed to the anisotonic solutions, (b) that sperm motility was reduced with either an increase or decrease of osmolality, and (c) that almost all sperm lost motility immediately after being exposed to any solution with an osmolality over 600 mOsm or below 120 mOSM.

Figure 2:
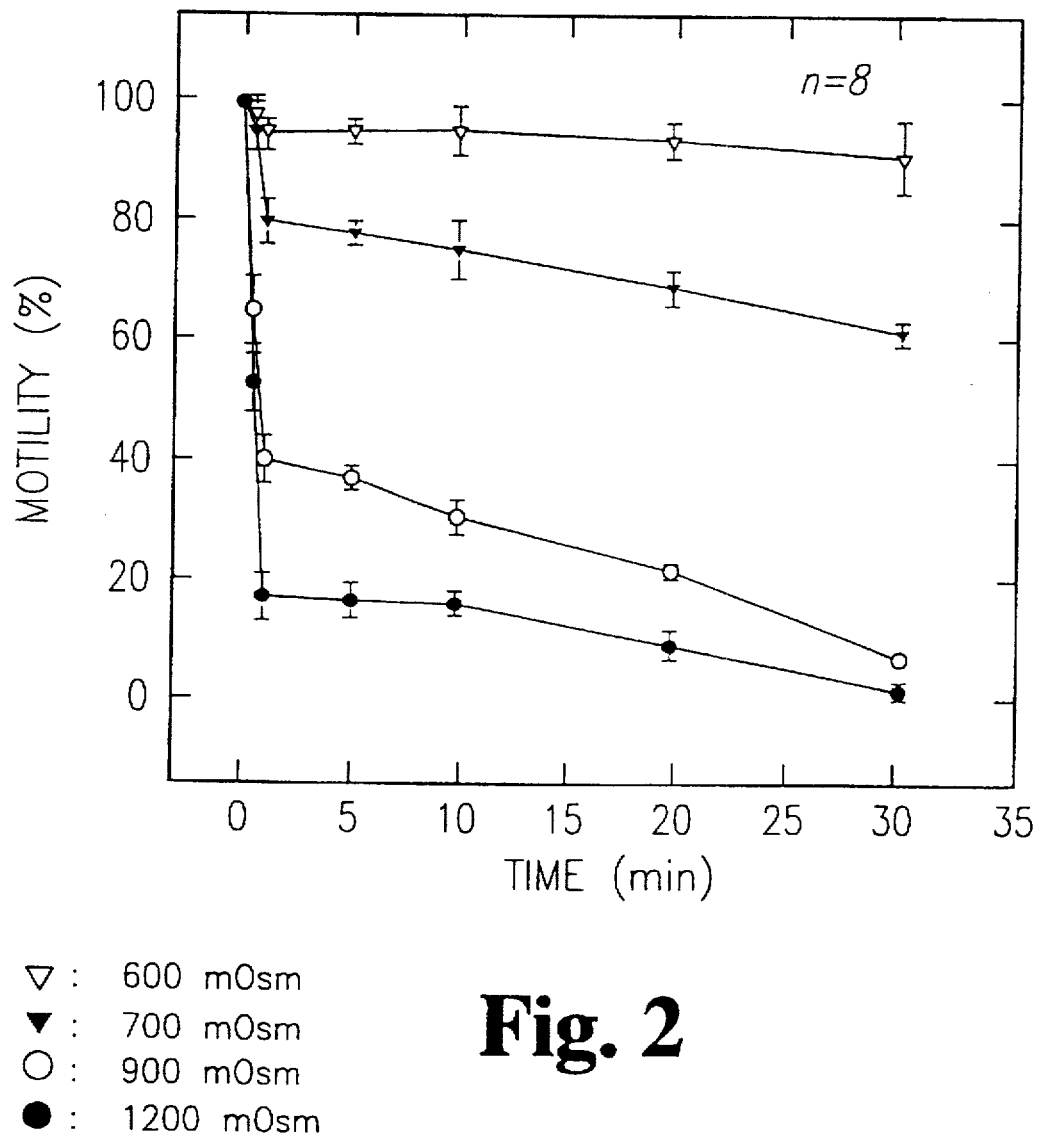
Figure 2A:
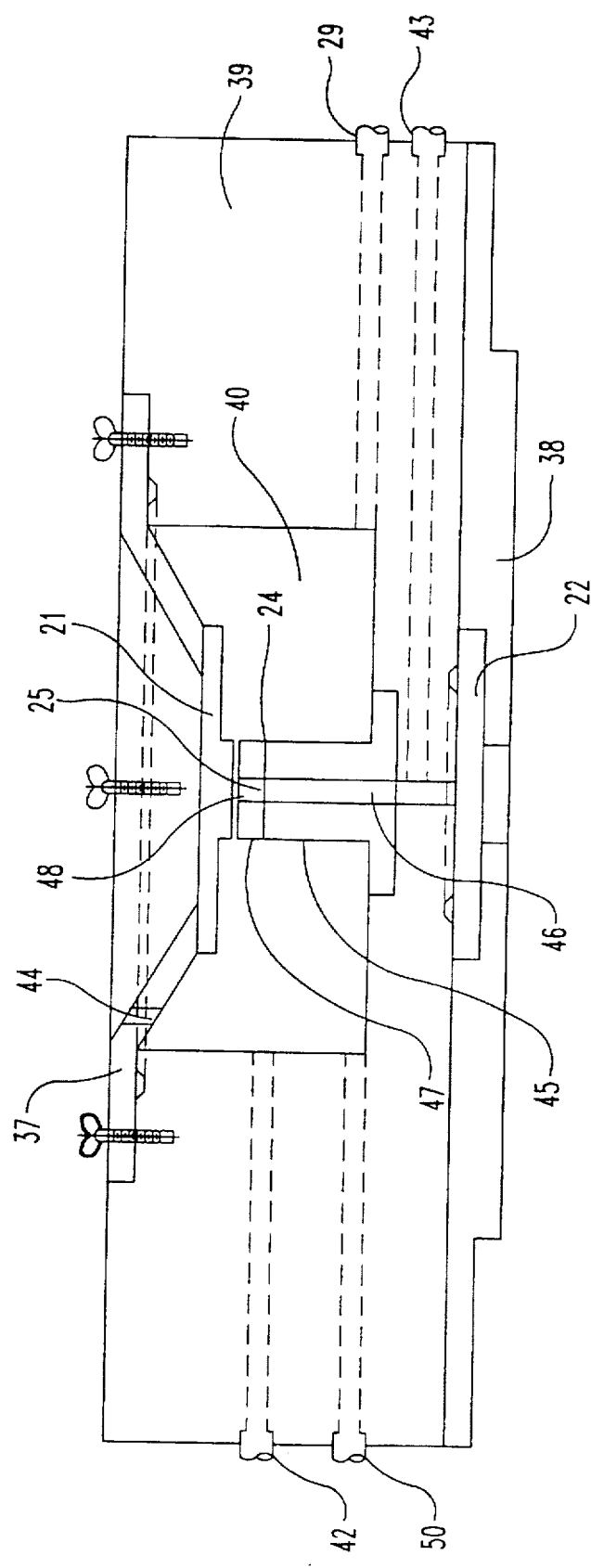
Figure 4:
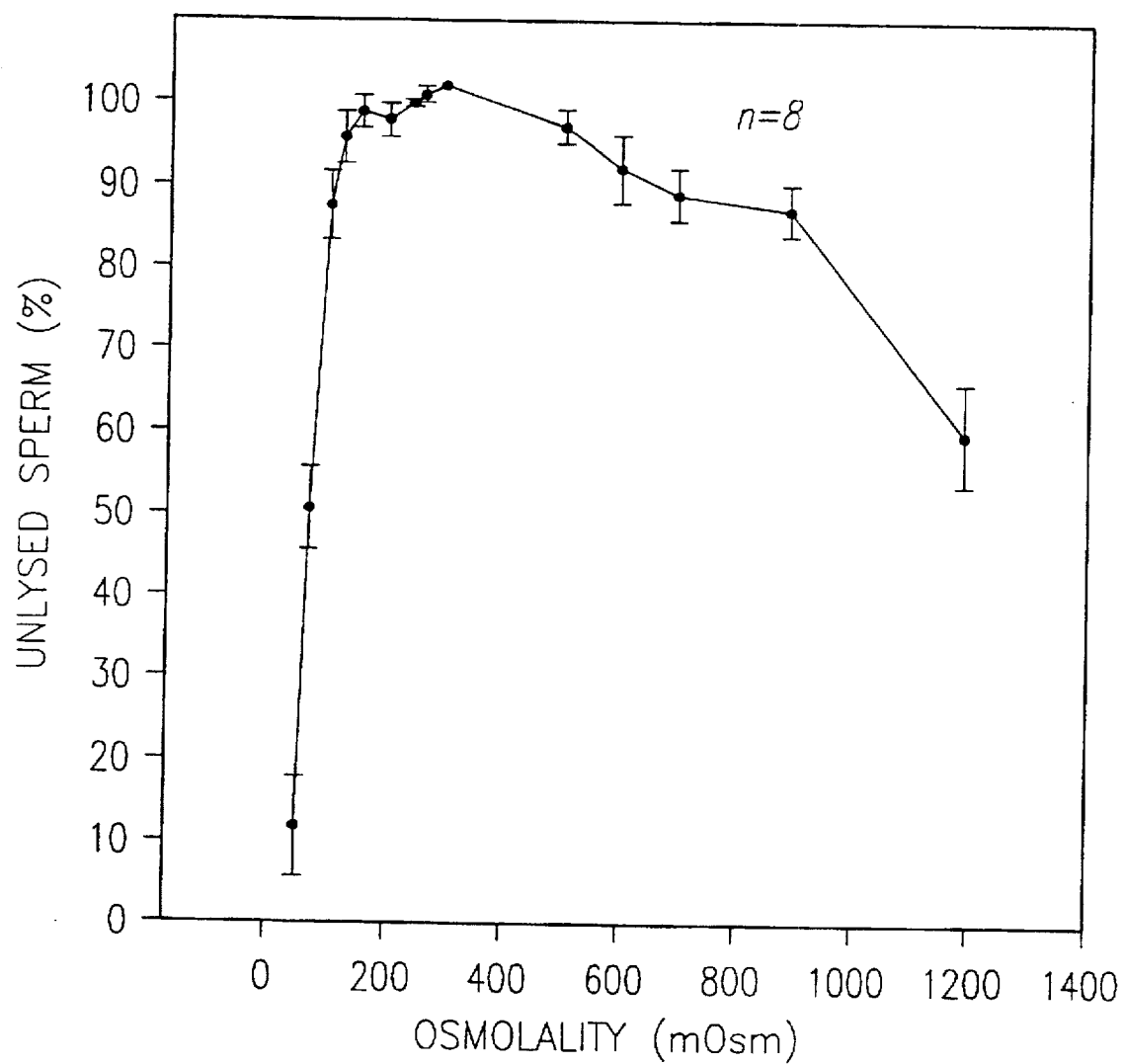

FIGS. 2 and 3 show post-hyperosmotic and post-hyposmotic sperm motility as a function of osmolality and as a function of time of sperm exposure to the anisosmotic conditions. FIG. 4 shows that the plasma membrane integrity of the human sperm returned to isosmotic conditions after a 10-minute exposure to the anisosmotic conditions. From FIGS. 2 to 4, motility was found to be substantially more sensitive to anisotonic conditions than membrane integrity, and motility was found to be more sensitive to hypotonic conditions than to hypertonic conditions. For example, exposure to 190 mOsm rendered half the sperm non-motile (FIG. 3), whereas half the sperm lost membrane integrity only when the osmolality was lowered to near 60 mOsm (FIG. 4). Most of the motility loss in hyposmotic conditions occurred within 1 sec (FIG. 3), with a slow further decline over the next 20 sec. The first apparent loss in motility in sperm, where sperm were exposed to hypertonic conditions and returned to isotonic conditions, occurred at 600 mOsm (FIG. 2), with more than half being rendered non-motile by a 1 minutes exposure to 900 mOsm. There was again a slow further decrease in motility as the exposure time was extended.

Figure 5:
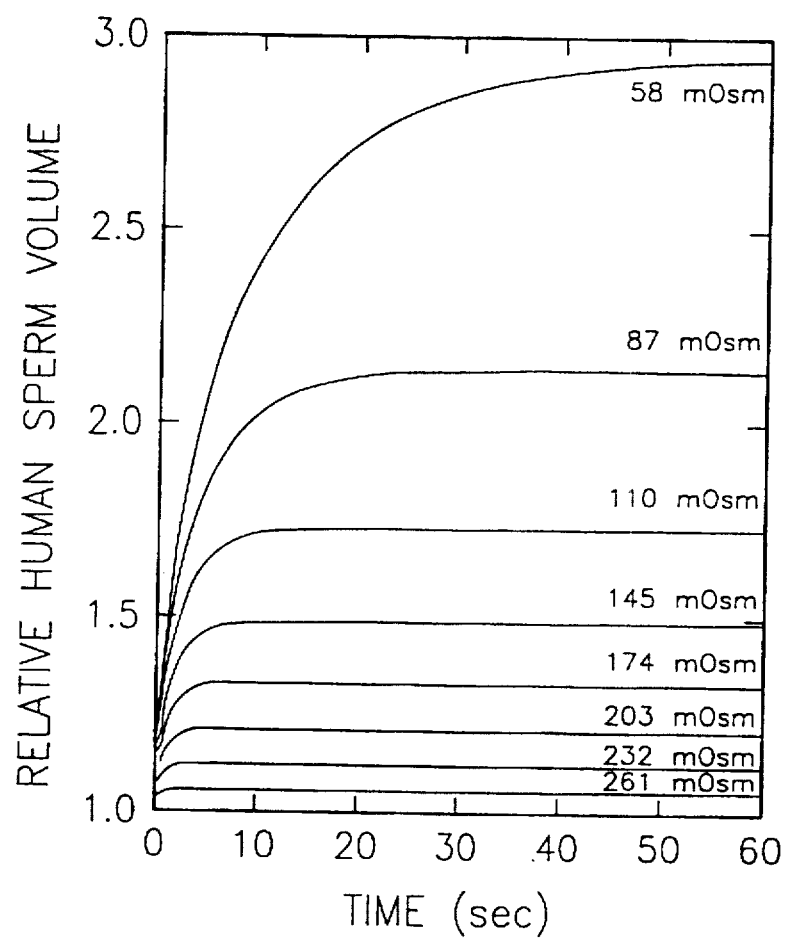
FIGS. 5 to 8 are graphical portrayals of examples of calculated sperm volumes as a function of osmolality.
Figure 6:
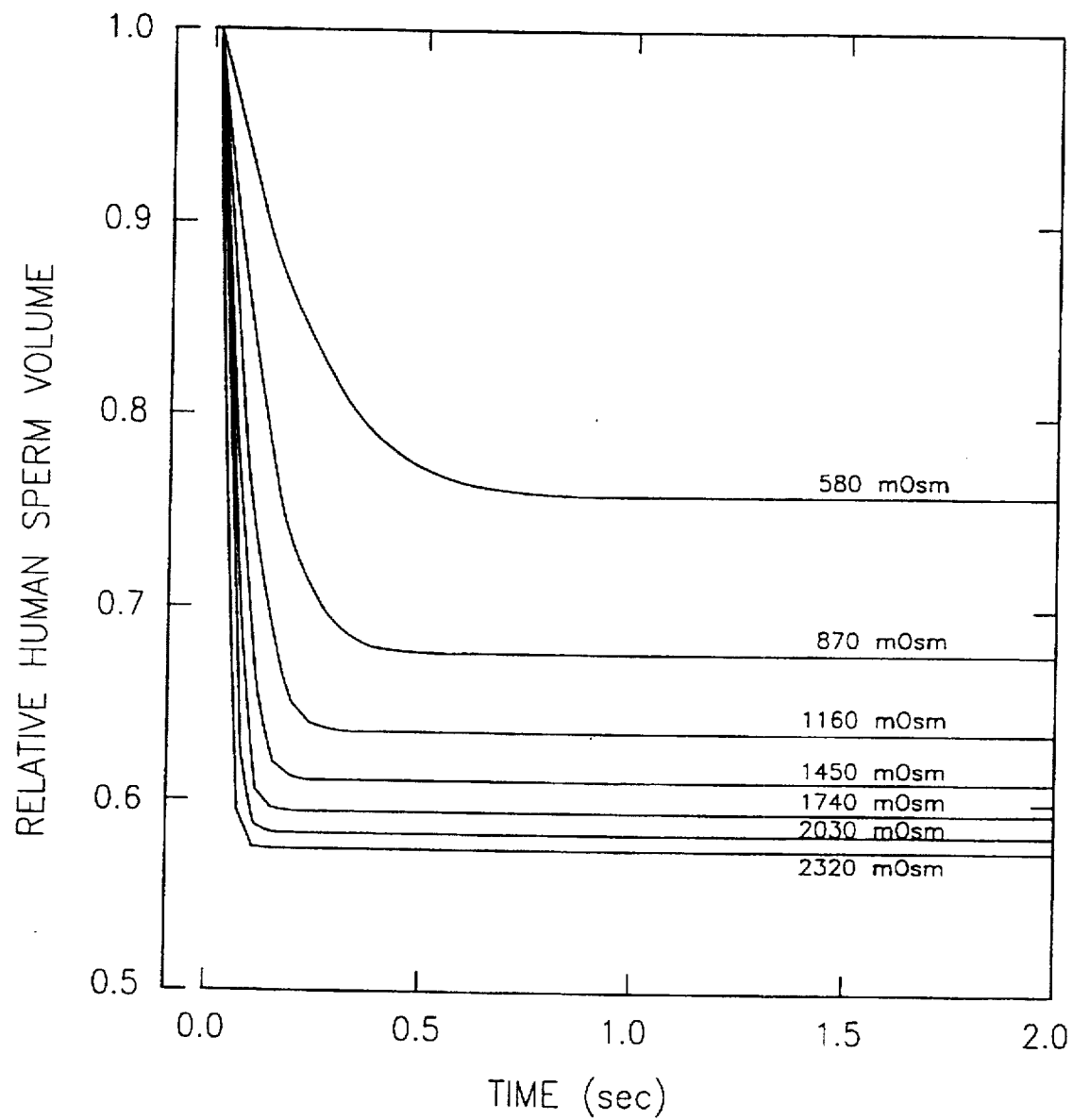

FIGS. 5 and 6 respectively show the predicted volume changes of the sperm after exposure to hypo- and hyper-osmotic solutions using equations 1 to 4 on this system. Based on the calculations performed, it was expected that human sperm shrank or swelled to osmotic equilibration volumes within one second (for shrinking) to a few seconds (for swelling).

In sum, from FIGS. 2 and 3, it was found that a part of the sperm irreversibly lost motility when returned to isotonic conditions after having been exposed to anisosmotic conditions. This post-anisosmotic motility loss was shown to be a function of both the exposure time and the osmolality. Since the anisosmotic solutions used contained only membrane-impermeable solutes, it was expected that sperm shrank or swelled when exposed to hyperosmotic or hyposmotic solutions. The shrunken or swollen sperm recovered their original volumes when returned to isotonic conditions.

A similar pattern, with the sperm's volume first shrinking or swelling and then recovering, takes place during the CPA addition or removal process from the sperm. Generally, when a cell is placed in a solution that is hyperosmotic with respect to the permeating solute (e.g. glycerol) but isotonic with respect to the impermeable salts, it first shrinks because of the osmotic efflux of intracellular water and then increases in volume as the solute (e.g. glycerol) permeates and as water concomitantly reenters the cell. When cells with CPA are exposed to an isotonic solution, they will swell because of osmotic influx of extracellular water and then decrease in volume as the CPA diffuses out of the sperm and as water concomitantly moves out.

Figure 7:
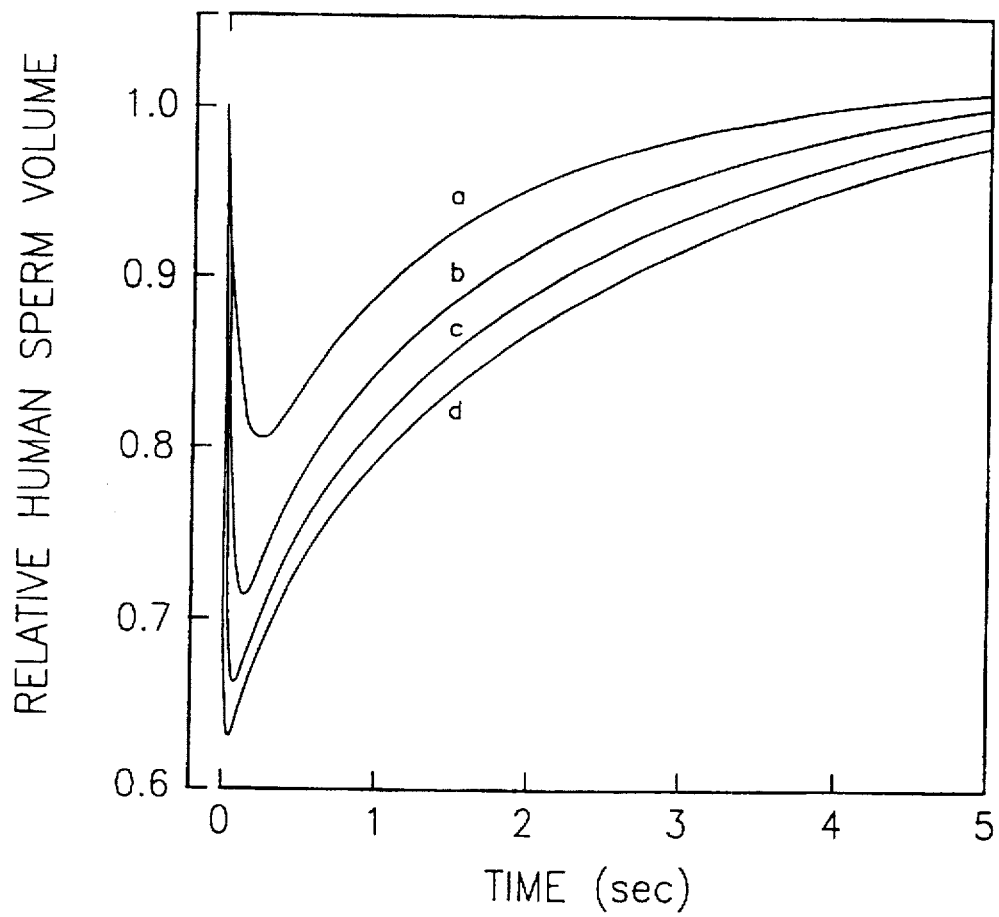
Figure 8:
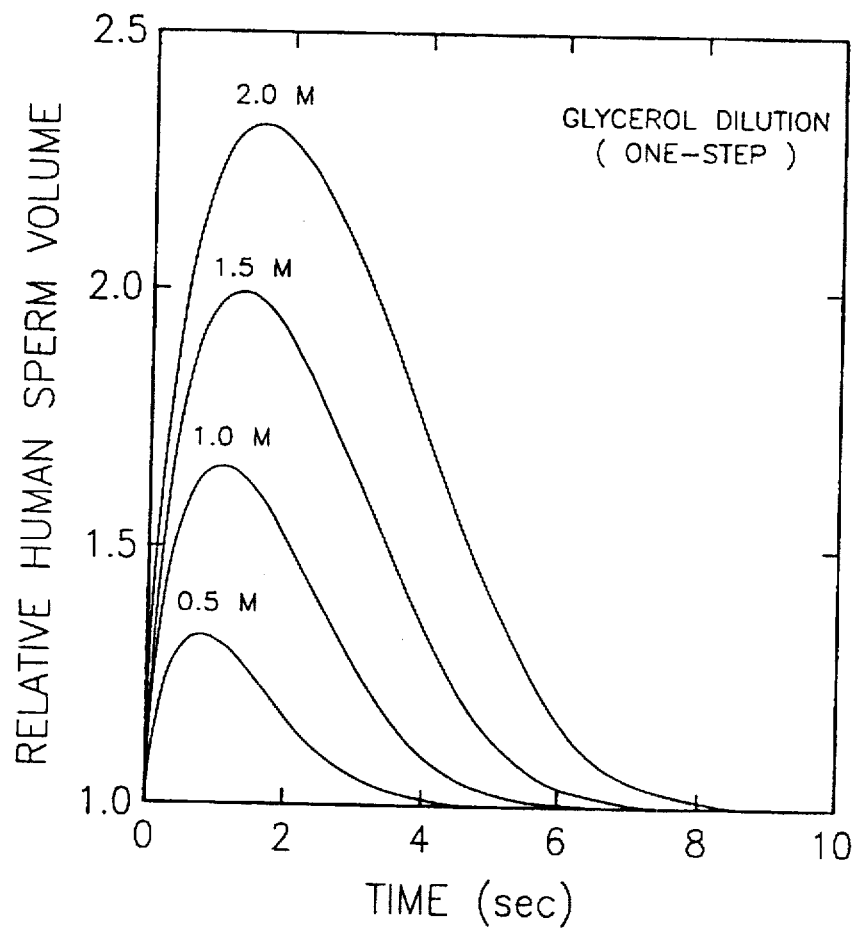

The sperm's volume changes during a 1-step addition and a 1-step removal of 9.5–2M glycerol were calculated from computer stimulation and are respectively shown in FIGS. 7 and 8. The higher the glycerol concentration, the longer the time period taken for the sperm volume recovery. However, typically it takes but a few seconds for human sperm to achieve their osmotic equilibration volumes. This means that the sperm experience the shrunken or swollen states for only an order of seconds during the addition or removal of glycerol. Therefore, the information concerning post-anisosmotic tolerance of the sperm returned to isotonic conditions after a short time exposure (an order of seconds) to the anisosmotic conditions is particularly important for designing optimal CPA addition/removal procedures to prevent sperm osmotic injury.

Figure 9:
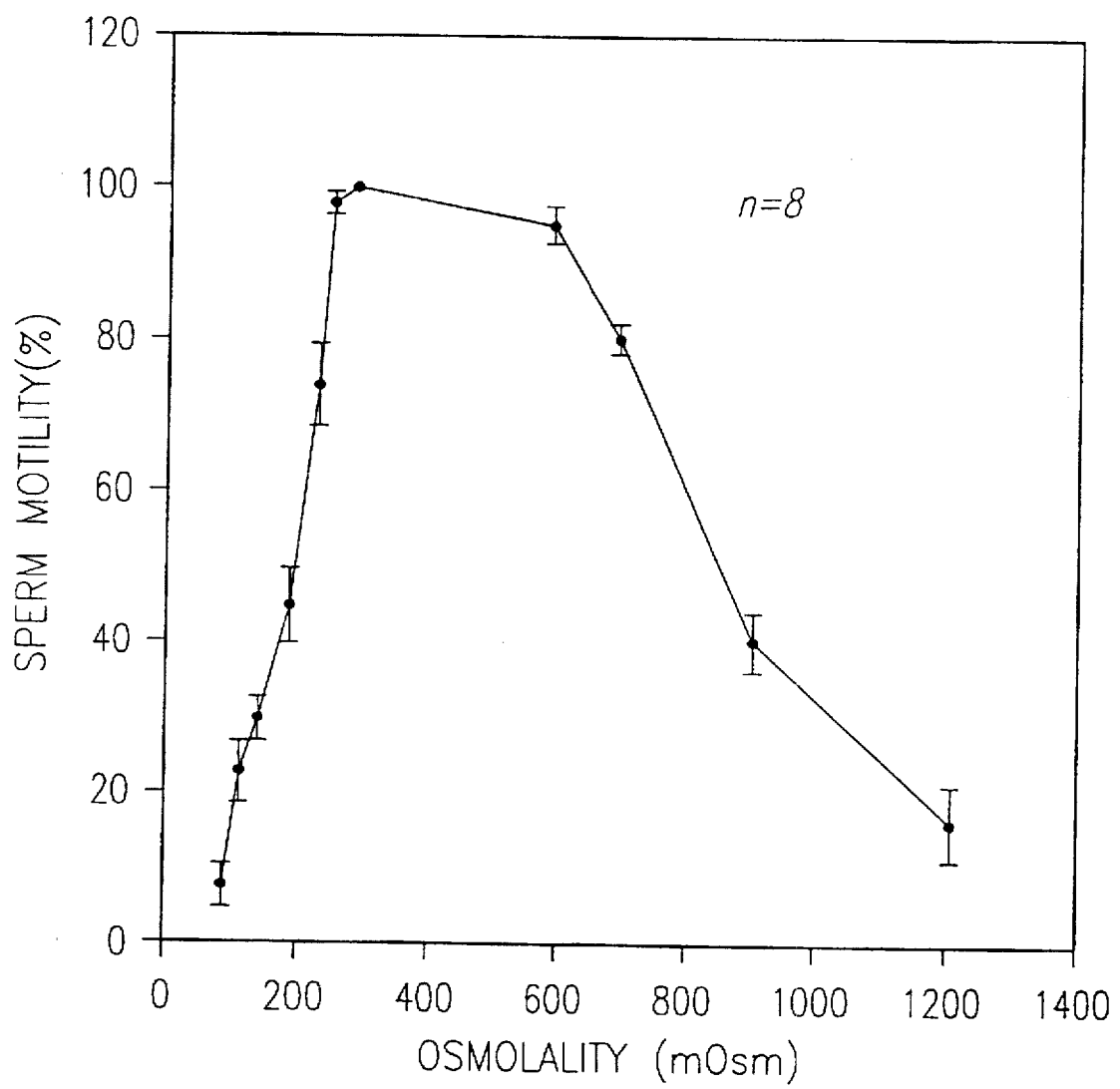
FIG. 9 is a graphical portrayal of an example of injury to sperm cells as a function of osmolality.

This information is obtained from FIGS. 2 and 3 which show the post-anisosmotic motility loss of the sperm as a function of the osmolality and the exposure time. Based on FIG. 2 and 3, the post-anisosmotic motility of human sperm with a short time exposure (an order of seconds) to anisosmotic conditions is summarized in FIG. 9 as a function of osmolality. To obtain a high (over 95%) motility recovery, the highest and lowest osmolalities which the human sperm can tolerate for a short time were found to be close to 600 mOsm and 240 mOsm, respectively (FIG. 9). Using these two osmolalities, the corresponding cell volumes were calculated using equation 3 or estimated from FIG. 5 and 6 to be approximately 0.75 (75%) and 1.1 (110%) times of isotonic human sperm volume, (values from FIGS. 5 and 6 being derived from the van't Hoff equation). This indicates that the sperm can only swell or shrink in a relative narrow range for a relative short time to avoid the motility loss. Again, the determined sperm volume limits are:

Upper Volume Limit (UVL): 1.1×isotonic sperm volume
Lower Volume Limit (LVL): 0.75×isotonic sperm volume Example 2

Prediction of Optimal Conditions for Glycerol Addition or Removal

The kinetics of water and glycerol transport across the sperm membrane were modeled using standard computing techniques that are well within the skill of the art of this invention and using Equations 1 to 4. Two preferred schemes of CPA addition, Fixed-Volume-Step (FVS) and Fixed-Molarity-Step (FMS), were analyzed in this regard and are presented below.

Figure 10:
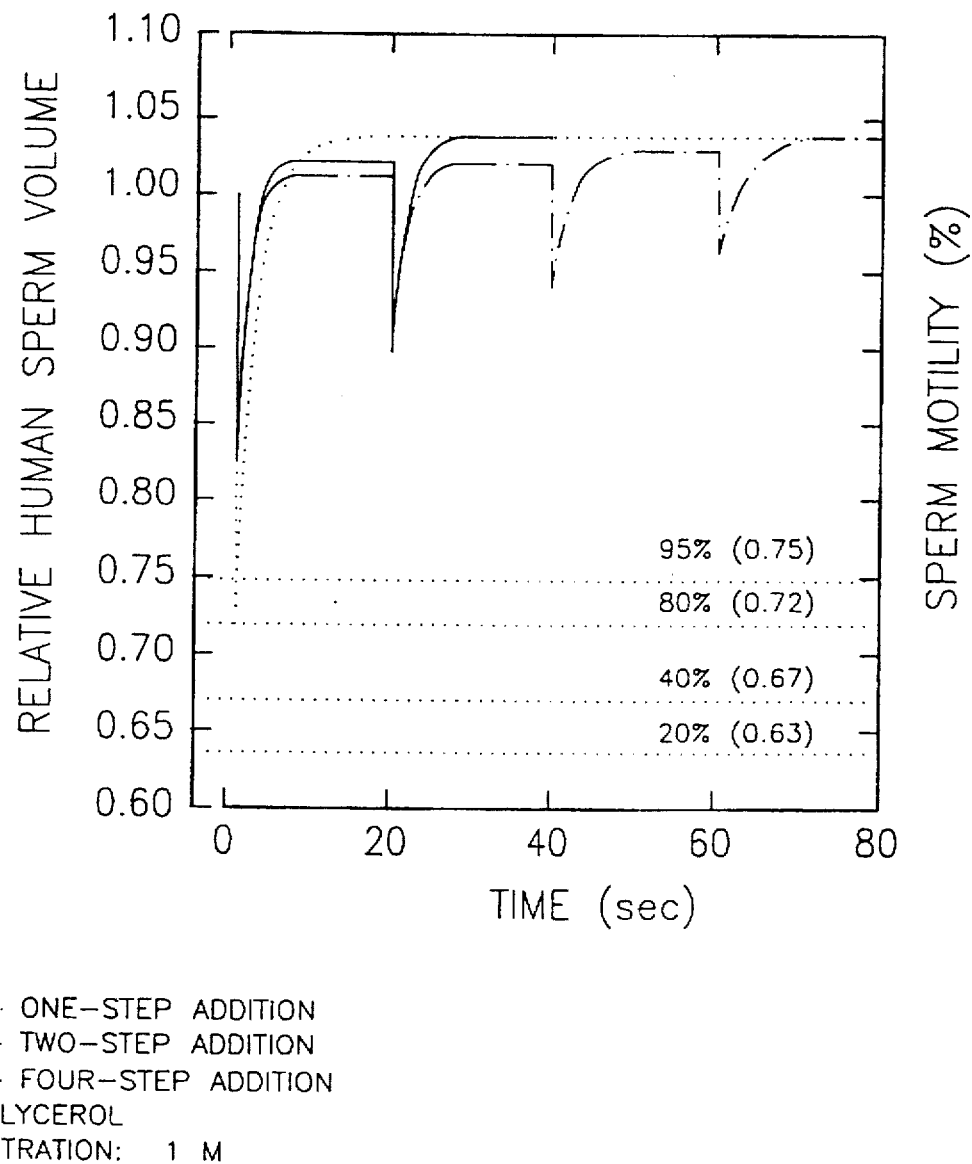
FIGS. 10 to 14 are graphical portrayals of examples of calculated sperm volumes as a function of osmolality.

Referring to FIG. 10, there is shown the calculated sperm volume change arising during a one-step, a two-step, and a four-step addition of glycerol to achieve a final 1M glycerol concentration at 22° C. using an FMS addition.

Figure 11:
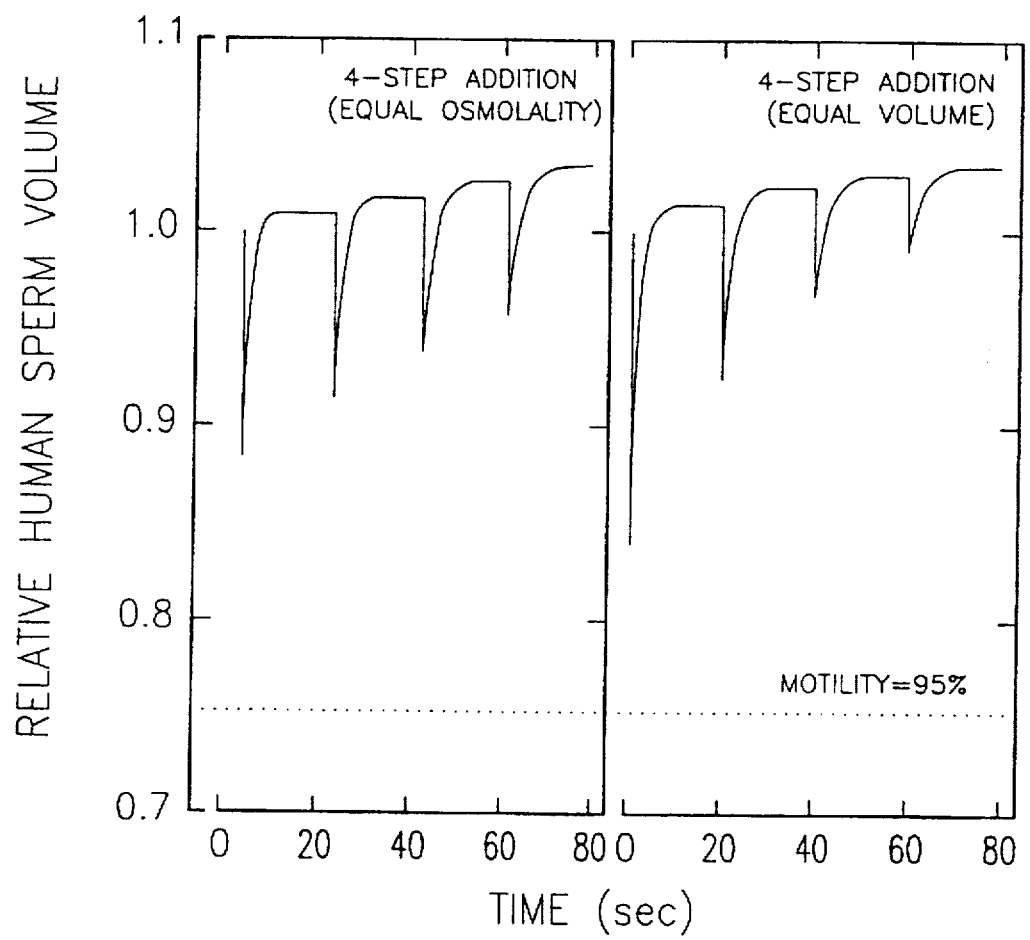

Referring to FIG. 11, there is shown a comparison between a four-step FVS addition of glycerol and a four-step FMS of glycerol.

From FIGS. 9 to 11, a one-step addition of glycerol to sperm is predicted to cause a 10% to 20% sperm motility loss. This loss is predicted to occur because the minimum volume which the sperm can attain during this addition is approximately 72% of the original cell volume, a value less than the minimally acceptable LVL of 75% previously determined above. In contrast, a four-step FVS or FMS addition of glycerol was predicted to greatly reduce such sperm motility loss (less than 5%).

Figure 12:
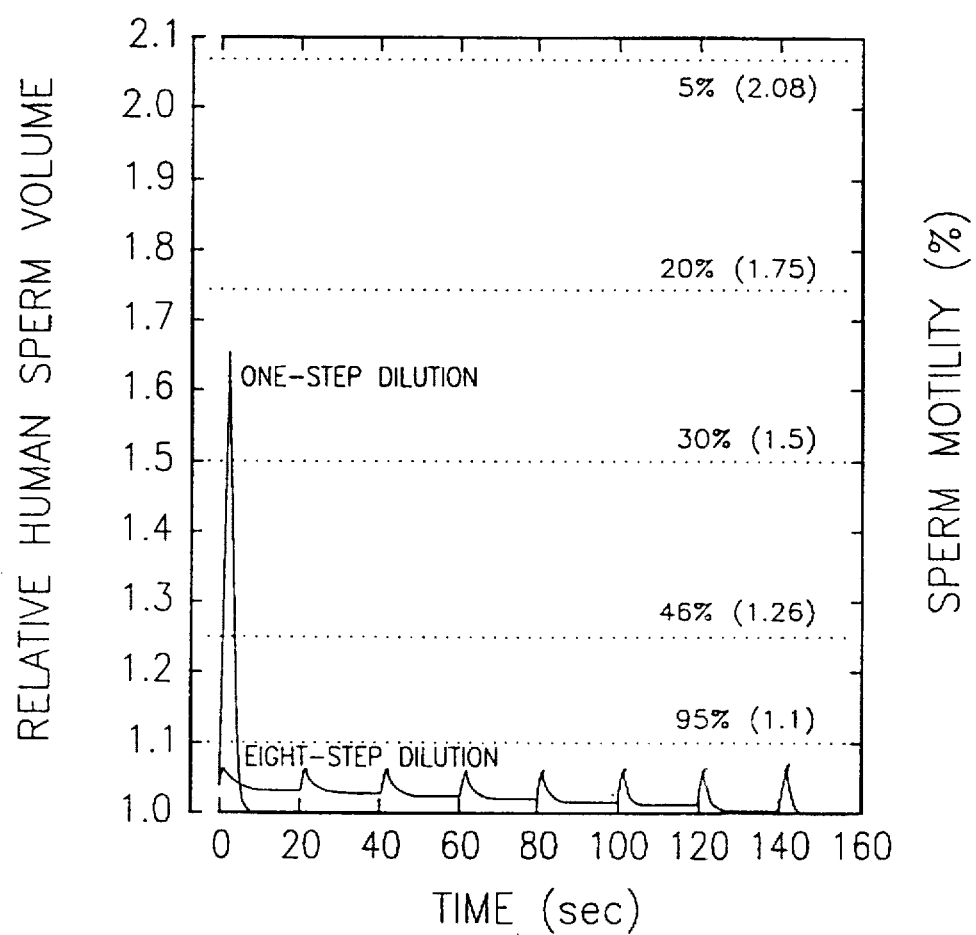

Referring to FIG. 12, there is shown a one-step removal of glycerol. This removal was predicted to cause as high as 70% motility loss because the maximum cell volume during the glycerol removal was calculated to be over 1.6 times larger than the isotonic cell volume, much higher than the upper volume limit of the sperm.

Figure 13:
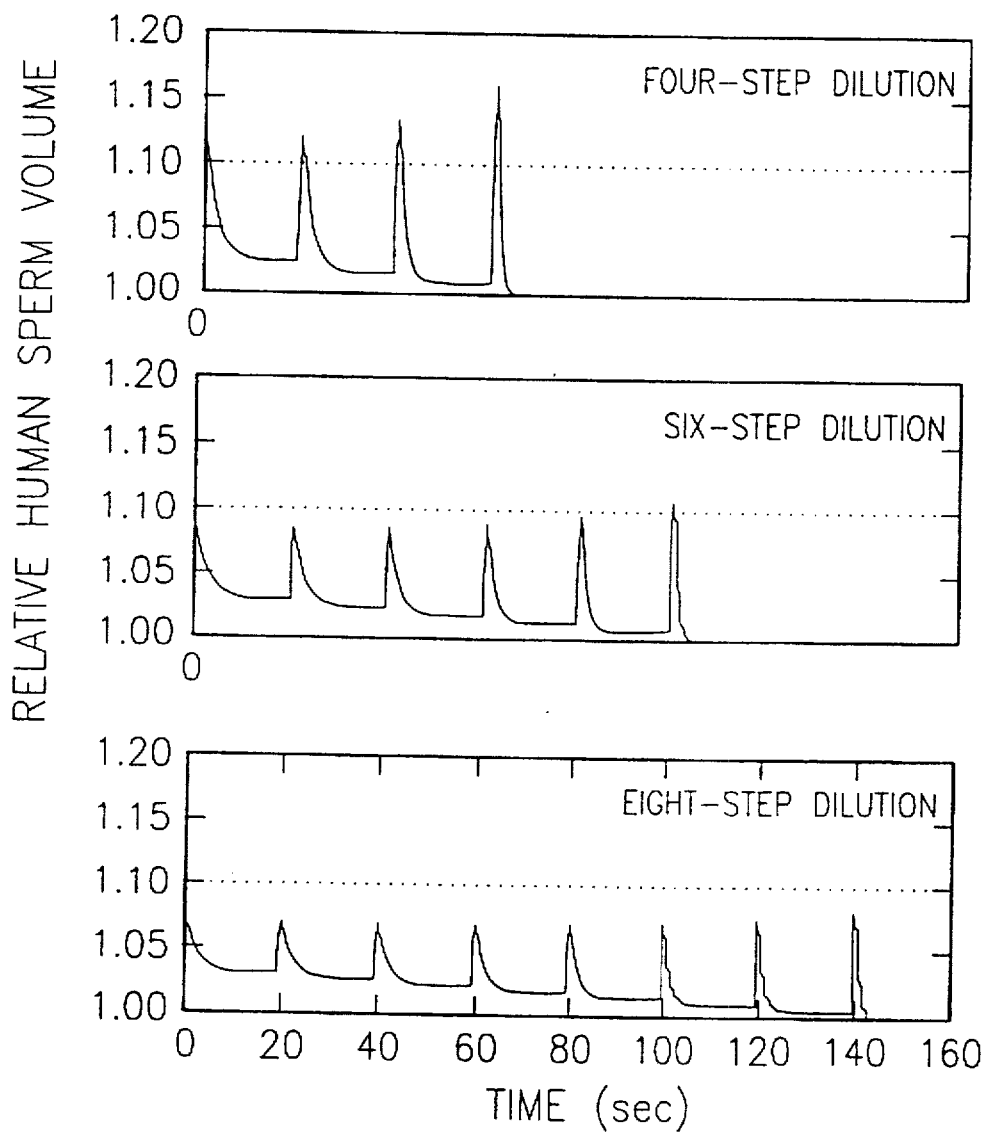

Referring to FIG. 13, there is shown a four-step, a six-step, and an eight-step FMS removal procedure. The four-step and six-step procedures were predicted to significantly reduce the sperm motility loss but still may cause over a 5% motility loss. An eight-step FMS removal was predicted to prevent sperm motility loss below the 5% level.

Figure 14:
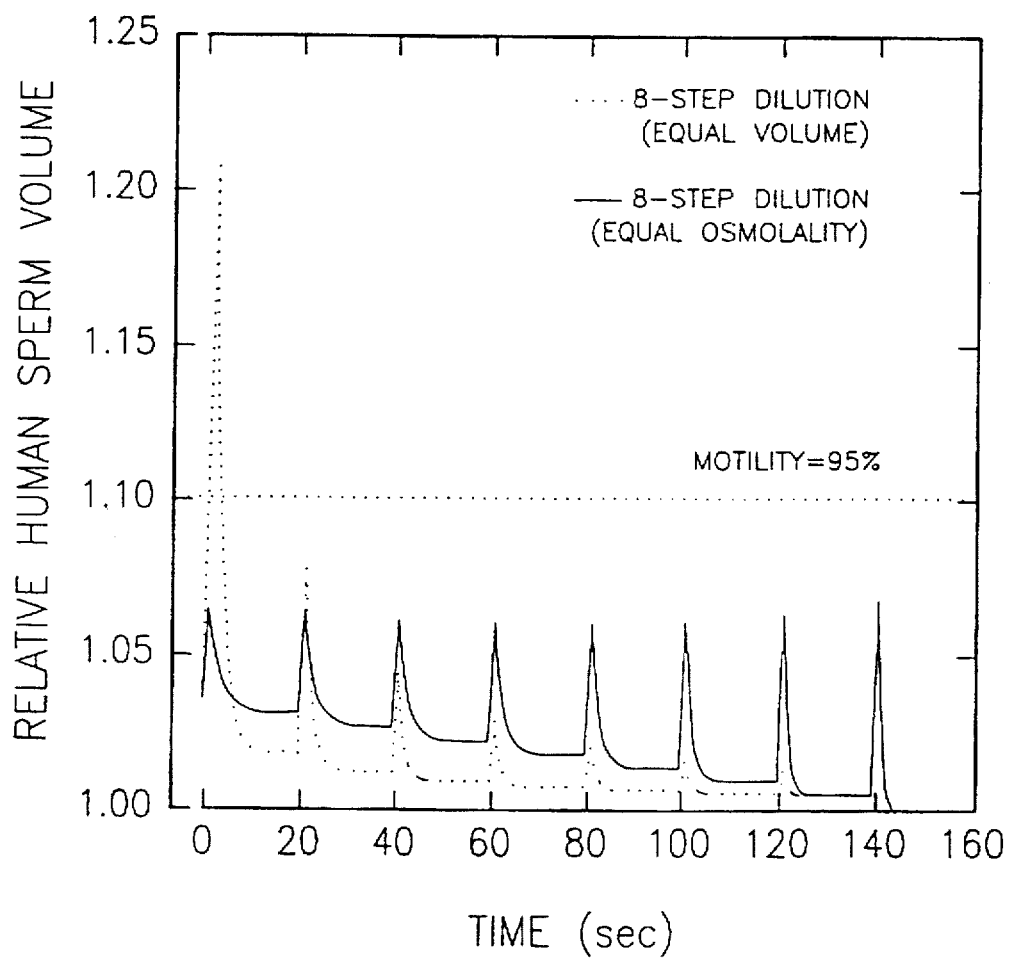

Referring to FIG. 14, there is shown a comparison between the eight-step FMS and the eight-step FVS removal procedures. The eight-step FMS removal was predicted to prevent sperm motility loss over the FVS procedure. An eight-step FVS removal was predicted to cause a maximum cell swelling of over 1.2 times higher than isotonic cell volume while FMS removal was predicted to be much lower than the UVL, indicating that the eight-step FVS removal is not as good as eight-step FMS removal. Also apparent from the computer simulation was the prediction that the human sperm would rapidly achieve an osmotic equilibrium (within seconds) during the 1-step or stepwise glycerol addition or removal. This further indicated that only a short time interval between steps of glycerol addition or removal was required.

In sum, a four-step FMS addition and and eight-step FMS removal of glycerol were predicted to be optimal protocols to prevent sperm motility loss in human sperm using the foregoing equations.

Figure 15:
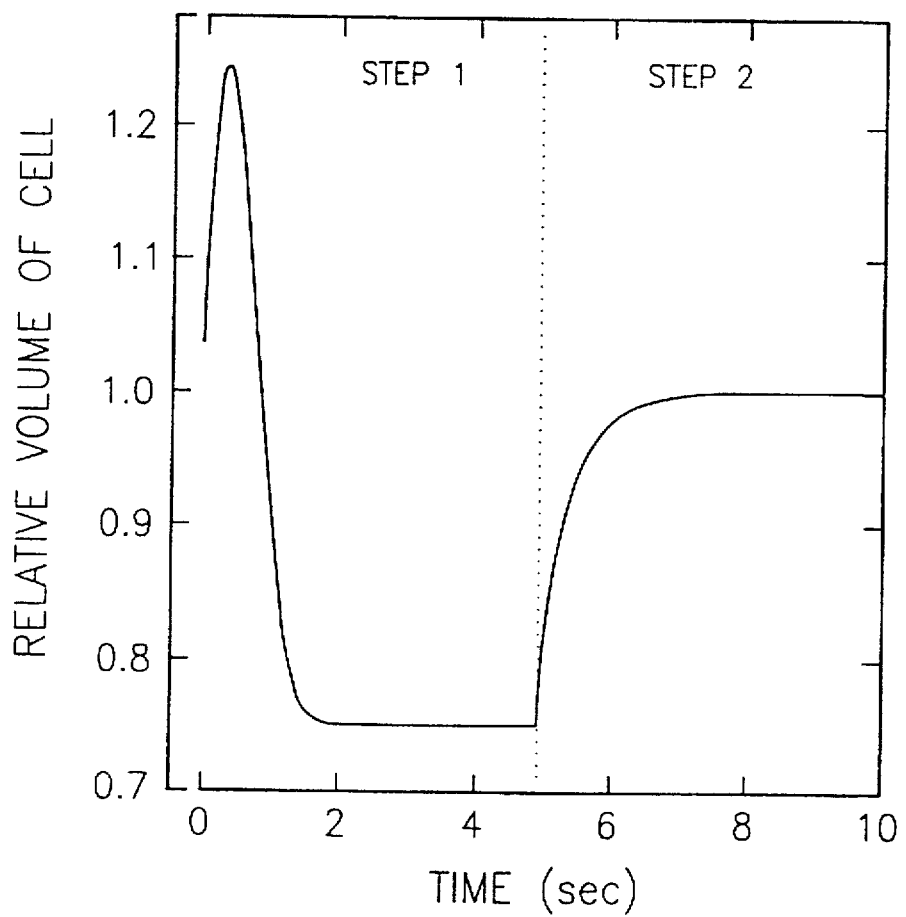
FIG. 15 is a graphical portrayal of an example of sperm cell volume change over time during a two-step removal of a cryoprotectant.

A two-step removal of CPA from the cells using a nonpermeating solute as an osmotic buffer has been previously used to avoid the osmotic injury to other cell types. The detailed procedure is: (1) the CPA is directly removed from the cells by transferring cells to a hyperosmotic medium (osmotic buffer) containing no CPA but only nonpermeating solutes, and then (2) the cells are directly transferred to an isotonic solution. It has been known that 600 mOsm is the hyperosmotic upper tolerance limit for human sperm (FIG. 9). Therefore, osmolality of the osmotic buffer medium should not be over 600 mOsm. Under this limit, a hyperosmolality of 600 mOsm is expected to provide the maximum "buffer effect" to reduce the sperm volume swelling during the first step of the "two-step" procedure for glycerol removal. Sperm volume change during the 2-step glycerol (1M) removal process using a 600 mOsm buffer medium was calculated and shown in FIG. 15. It was predicted that maximum volume of the sperm would achieve 1.25 times of the isotonic cell volume, which is higher than the UVL of the sperm, and might cause over 50% sperm motility loss.

Example 3

Examination of the Osmotic Injury Actually Found Using a Previously Modeled CPA Addition or Removal Procedures TL-HEPES medium with 2M glycerol was either one-step or stepwise added to an equal volume of the isotonic sperm suspension to achieve a final 1M glycerol concentration at 22° C. Glycerol in the sperm was removed by dilution either by a one-step or stepwise addition of the TL-HEPES medium with or without an osmotic buffer (sucrose) placed into the cell suspension. The detailed procedures for the glycerol addition and removal are described in Tables 2–5. Sperm motility before, during, and after the different glycerol addition and removal procedures was measured by CASA. The membrane integrity of the sperm was determined by the dual staining technique and flow cytometry.

TABLE 2

Procedures used in 4-step addition of 1 ml of 2M
glycerol solution of 1 ml of isotonic sperm suspension

| FVS | FMS |
| --- | --- |
| Add 0.25 ml of 2M glycerol 4 times to 1 ml isotonic sperm suspension | Stepwise add 0.14, 0.19, 0.27 and 0.4 ml of 2M glycerol to isotonic sperm suspension |

The time interval between two steps was approximately 1-2 minutes. The volume of solution added in each step was calculated using Equations 5 or 6.

TABLE 3

Procedures used in 1-step and 8-step
removal of 1M glycerol from the human sperm
8-Step Dilution

| FVS | FMS |
| --- | --- |
| Add 100 µl of isotonic TALP 7 times to sperm suspension to achieve a final glycerol concentration, 0.125M. After centrifugation, 710 µl of supernatant was taken Remaining cell suspension volume is 90 µl | Stepwise add 14.3, 19, 26.6, and 40 µl of isotonic TALP medium to 100 µl of sperm suspension with 1M glycerol; (2) centrifuge the cell suspension at 400 g for off. 5–7 minutes.; (3) take off 170 µl of the supernatant; Stepwise add 10, 20 and 60 µl of isotonic solution to the remaining 30 ul of sperm suspension. After the above 7 steps dilution, the glycerol concentration in the sperm suspension is 0.125M. The final suspension volume is 90 µl |

The final 90 µl of sperm suspension were further diluted by adding 180 µl of TALP solution for the CASA analysis. The time interval between two steps is approximately 1–2 minutes. The volume of diluent added in each step was calculated using Equations 7 or 8.

One Step Dilution

Add 2000 µl of isotonic solution directly to 100 µl of cell suspension with 1M glycerol.

Table 4

Procedures used in 2-step removal of 1M glycerol from the human sperm using sucrose as an osmotic buffer (1) Add 2000 µl of sucrose buffer medium (TALP+ sucrose, 600 mOsm) to 100 µl of sperm suspension with 1M glycerol; (2) centrifuge the suspension (400 g for 7 minutes) and take off the supernatant; and (3) resuspend cell pellet with 500 µl isotonic TALP medium.

Results from Experimental Examination

Figure 16:
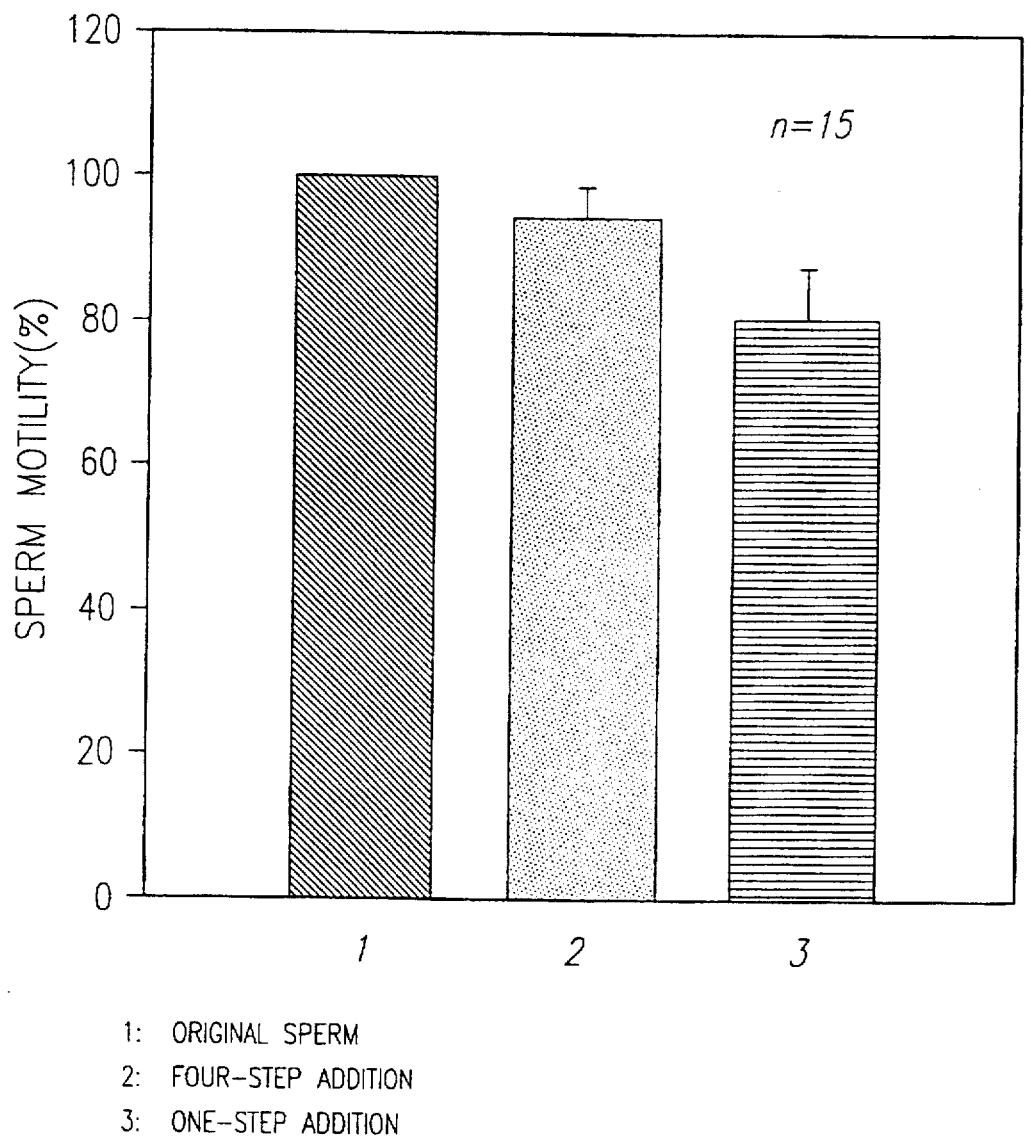
FIGS. 16 to 18 are graphical portrayals of examples comparing injury to sperm cells using various schemes of cryoprotectant addition or removal.
Figure 17:
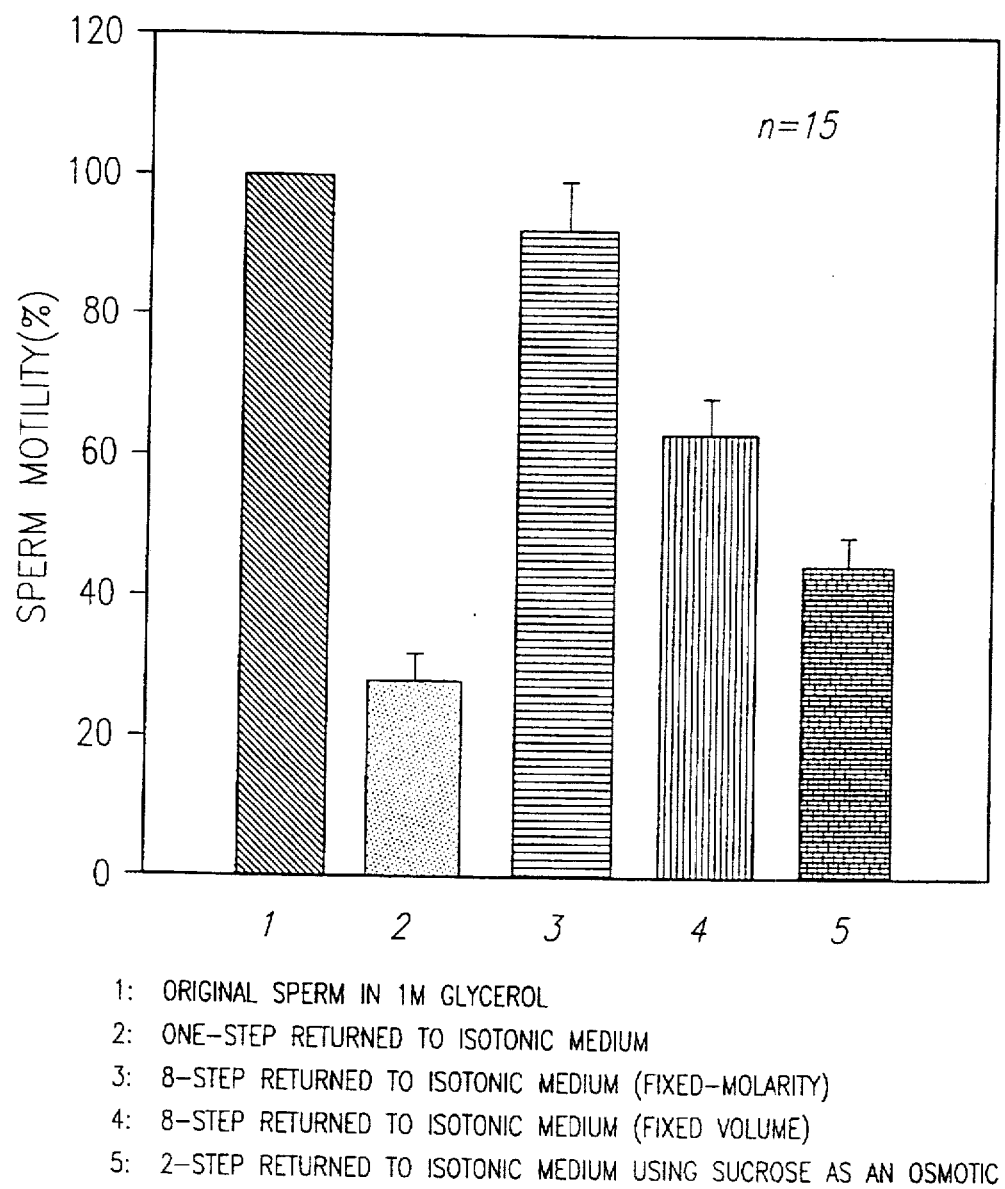

Glycerol was experimentally added to or removed from the human sperm using the stepwise procedures as predicted from the computer simulation. Percent motility of the human sperm after one step or a four-step FMS addition of glycerol (Table 2) is shown in FIG. 16. One step addition created approximately 20% sperm motility loss while the four-step addition, less than 8%. FIG. 17 shows effects of different glycerol removal procedures (Table 3) on the human sperm motility loss. Less than 30% motile sperm kept motility after one-step removal of glycerol while majority of sperm (over 92%) maintained the motility after the eight-step FMS removal. The motility loss caused by a two-step removal of glycerol using sucrose as a non-permeating buffer (total osmolality of the buffer medium was 600 mOsm) was close to 45%. Thirty-five percent of the sperm lost motility after a eight-step FVS removal of glycerol. The experimental results agree well with the predictions generated from computer simulation.

Figure 18:
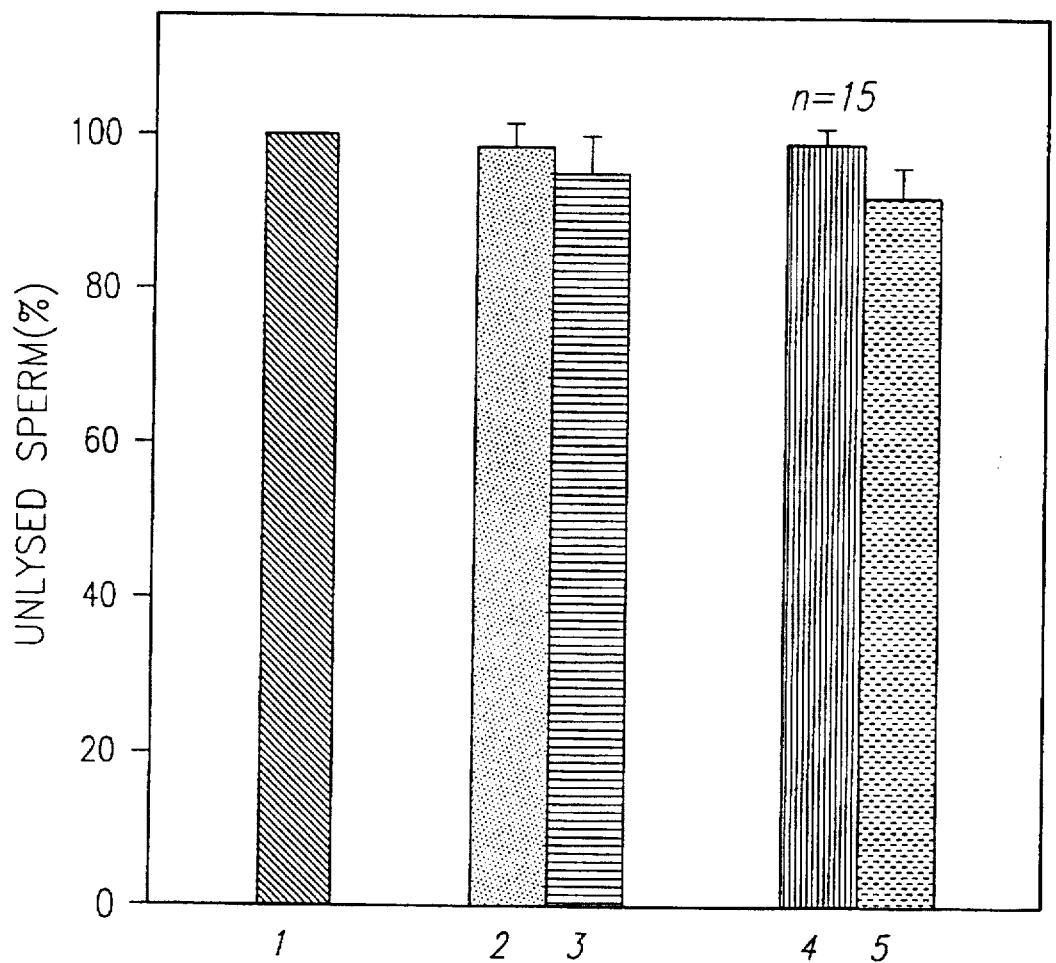

FIG. 18 shows the membrane integrity of the human sperm in 1M glycerol solution or after addition and removal of 1M glycerol by the different procedures. The sperm appeared to maintain membrane integrity under all experimental conditions.

DISCUSSION

The addition of CPA to the sperm before cooling and its removal from sperm after warming are two of very important procedures in sperm cryopreservation. The present invention offers a new methodology to define optimal procedures to carry out either or both of these procedures in a fashion to reduce osmotic injury of the sperm. The calculated procedures were implemented and the results agree remarkably well with prediction.

This example presented two CPA addition or removal schemes (FVS and FMS). As the example shows, the Fixed-Molarity-Step is preferable to reduce osmotic injury over the Fixed-Volume-Step. In particular, for human sperm, the example shows that a four-step FMS addition of glycerol to the sperm and an eight-step FMS removal of glycerol from the sperm were predicted to be optimal, which was confirmed upon implementation. Upon reviewing each scheme, the minimum/maximum cell volumes after each step of FVS addition/removal was uneven or unequal, some of which exceeded the LVL and UVL of the sperm. In contrast, minimum/maximum cell volumes after each step of FMS addition/removal of glycerol were shown to be relative even (FIGS. 11 and 14). For a fixed number of steps, the extent of cell volume change during CPA addition/removal using the FMS scheme is much smaller than that using the FVS scheme (also see FIGS. 11 and 14).

A careful review of the foregoing methodology demonstrates that in the preferred practice of this invention, the sperm cell volume change will be kept in a range which the sperm cells can tolerate during the addition or removal of the cryoprotective agent. For an example, a preferred method to remove cryoprotectant would swell the sperm cells to at least 90% of the upper volume limit (i.e. 0.9 times the upper volume limit) but not substantially exceed the upper cellular volume limit. For another example, a preferred method to add cryoprotectant would shrink the sperm cells to at least 110% of the lower volume limit (i.e. 1.1 times the lower volume limit) but not substantially drop below the lower cellular volume limit. However, the total number of steps for tie addition/removal and the time required for completing the addition/removal are also important because of potential chemical toxicity CPA can have upon unfrozen sperm. Generally speaking, CPA should be added into or removed from sperm as soon as possible before cooling or after warning to eliminate long periods of exposure to CPA at relatively high temperatures. Any action to limit such exposure requires the least number of steps for the addition or removal of the CPA. Thus, this is a second feature for developing an optimal procedure for the addition/removal of CPA.

Accordingly, tie preferred stepwise procedure for CPA addition/removal will (1) keep sperm cell volume in an accepted range and (2) reduce the total number of steps required to add/remove the CPA. To achieve this goal, the following two criteria can be taken into account in computer simulation to predict the optimal procedures: (a) the maximum/minimum cell volume during each step of CPA addition/removal must be constant and (b) the maximum/minimum cell volume must be close to (not exceed) the UVL and LVL of the sperm cells. Although the FMS scheme is shown in the foregoing examples to be better than the FVS, it still did not completely satisfy the criterion (a) (see FIGS. 11 and 14). Using computer simulation, a practitioner in the art can use the information in this specification to further customize a protocol specifically for their needs, e.g. better satisfy both criteria (a) and (b).

An important step to practice this invention is to determine the osmotic tolerance of the sperm cells. However, these limits are effected by the assays used to evaluate sperm viability. For example, see Example I, sperm motility was used as a standard of sperm viability because of relatively high sensitivity of the sperm motility to the osmotic change and the requirement of sperm motility for most clinical applications. Other characteristics of sperm may be similarly used to determine appropriate protocols, which may offer different osmotic tolerance limits.

Finally, it should be remembered that the effect of potential chemical toxicity of CPA on sperm cell viability is another reason causing sperm cell injury during the addition and removal of CPA for sperm cell cryopreservation. Given a CPA type and CPA concentration, it is generally accepted that the potential toxicity of the CPA to the cells is decreased with a decrease of cell exposure time to the CPA and a decrease in temperature.

END OF EXAMPLES

A further aspect of this invention is the selection of a membrane or a membrane and its associated device to add or remove a cryoprotective agent at a predetermined rate that does not allow a biological cell to substantially exceed a predetermined volumetric limit. Given the predetermined volumetric limits of a cell type, the permeability coefficients of water and the cryoprotective agent of the particular cell membrane, and the reflection coefficient (if not assumed to be 1), various devices can be designed that add or remove a cryoprotective agent to a biological cell at a predetermined rate governed by the proper selection of a membrane. A proper membrane allows water or a cryoprotective agent to contact the biological cells at a rate that by design will approach but riot allow the biological cells to substantially exceed their predetermined volumetric limits. Diffusion of both water and cryoprotectant through the membrane is controlled so that the cells are prevented from contacting cryoprotectant or water at a rate that makes them swell or shrink beyond the predetermined limits.

Figure 19:
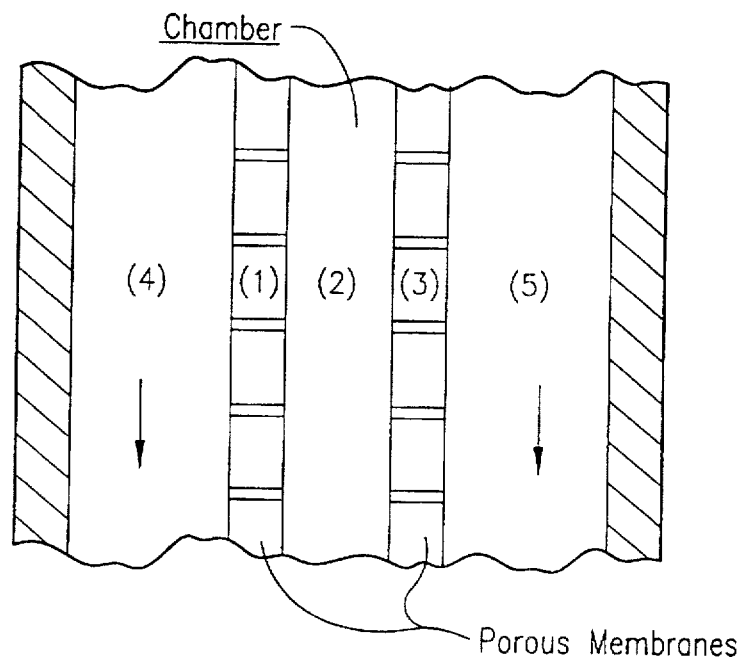
FIGS. 19 and 20 are cross-sections of a device to add or remove cryoprotectant from a cell type.

For example, a typical system for CPA removal is shown in FIG. 19. A cell suspension with cryoprotectants is placed in the chamber (region 2) with an internal space/thickness of L. Two walls of the chamber are the porous membranes (regions 1 and 3) with special characteristics (e.g. membrane thickness: 150 μm, pore size: 0.22 to 0.65 μm in diameter, pore area: 70% of the total membrane surface area). For removing CPAs, isotonic cell culture medium without CPAs are continuously pumped and run through compartments (4 and 5) to quickly remove CPAs diffusing from the chamber (region 2) through the porous membrane. Meanwhile, the isotonic medium diffuses into the chamber to dilute the CPA concentration in the cell suspension. Because the porous membrane used is a nonselective membrane (pore size 0.23 to 0.65 μm). CPAs and other solutes and solvents (water) diffuse freely across the cell membrane with a constant cell suspension volume in the chamber. The pore size of the porous membrane, the thickness of the cell chamber, the diffusibility of CPA in the solution, the permeability coefficients of the cell membrane to water and CPA are control factors used in the design of the system. Basic assumptions and mathematical formulation describing the CPA diffusion across the porous membrane and the change of CPA concentration distribution in the chamber (i.e., the extracellular environment) are as follows:

Basic Assumptions

1) One-dimensional transient mass transfer (developing mass transfer boundary layer is accounted for with a mean mass transfer coefficient $h_D$).

2) No net volume flow in the sample region 2.

3) Full-developed, steady-state laminar hydrodynamic conditions in the bulk flow regions 1 and 3.

4) The diffusion chamber is isobaric and isothermal.

5) Constant mass diffusivities.

6) Negligible solute and solvent velocities normal to the porous membrane.

Figure 20:
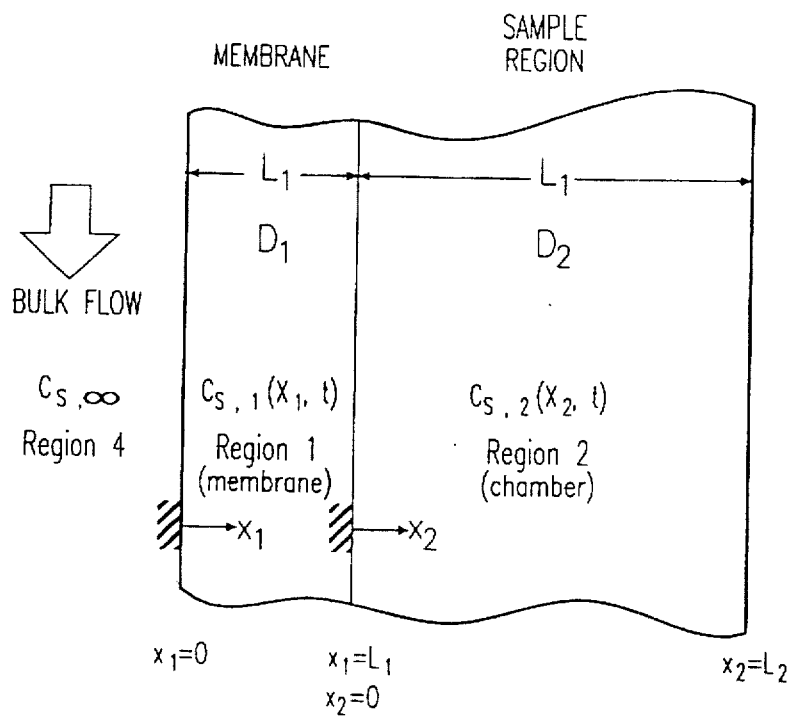

The problem considered therefore is one-dimensional transient diffusion through three adjacent regions (1, 2, and 3). Because of the symmetry of regions 1 and 3, only CPA diffusion in region 1 and half of region 2 needs to be considered. The following equations represent mathematical formulation of the CPA diffusion in region 1 and half of region 2 (FIG. 20):

$$\frac{\partial C_{s,1}(x_1,t)}{\partial t} = D_1 \frac{\partial^2 C_{s,1}}{\partial x_1^2} \quad 0 \le x_1 \le L_1; t>0 \quad (1)$$

$$\partial C_{s,2}(x_1,t) = D_2 \frac{\partial^2 C_{s,2}}{\partial x_2} \quad 0 \le x_2 \le L_2; t>0 \quad (2)$$

subject to the boundary conditions:

$$h_p[C_{s,\infty}(t) - C_{s,1}(0,t)] = D_1 \frac{\partial C_{s,1}(o,t)}{\partial X_1}$$

$$C_{s,1}(L_1,t) = C_{s,2}(0,t)$$

$$D_1 \frac{\partial C_{s,1}(L_1,t)}{\partial X_1} = D_2 \frac{\partial^2 C_{s,2}(0,t)}{\partial X_2^2}$$

$$\frac{\partial C_{s,2}(L_2,t)}{\partial X_2} = 0$$

and the initial conditions:

$$C_{s,1}(X_1,0) = C_i$$

$$C_{s,2}(x_2,0) = C_i$$

$$C_{s,\infty} = C_i, t<0$$

where $C_s$ is the CPA concentration, subscripts $_1$ and $_2$ represent region 1 and region 2, respectively. D is the diffusivity of the given CPA, t is time, x is position, $h_D$ is the convective mass transfer coefficient of the CPA, $C_{s,\infty}$ is the CPA concentration in the bulk flow in compartments (4 or 5). $C_i$ is the initial concentration of the CPA.

A solution is sought for the case where a step change in the convective flow concentration $C_{s,\infty}$ occurs. At time t=0, $C_{s,\infty}$ is assumed to change instantaneously to $C_f$, which is assumed to be constant (=0, i.e. CPA concentration in the compartments is so low as to be negligible). As a first approximation, D1 is assumed to be D2×f, where f is the fraction of membrane pore area over the total membrane surface area (70% in the porous membranes used and tested), L2=L/2.

Figure 21:
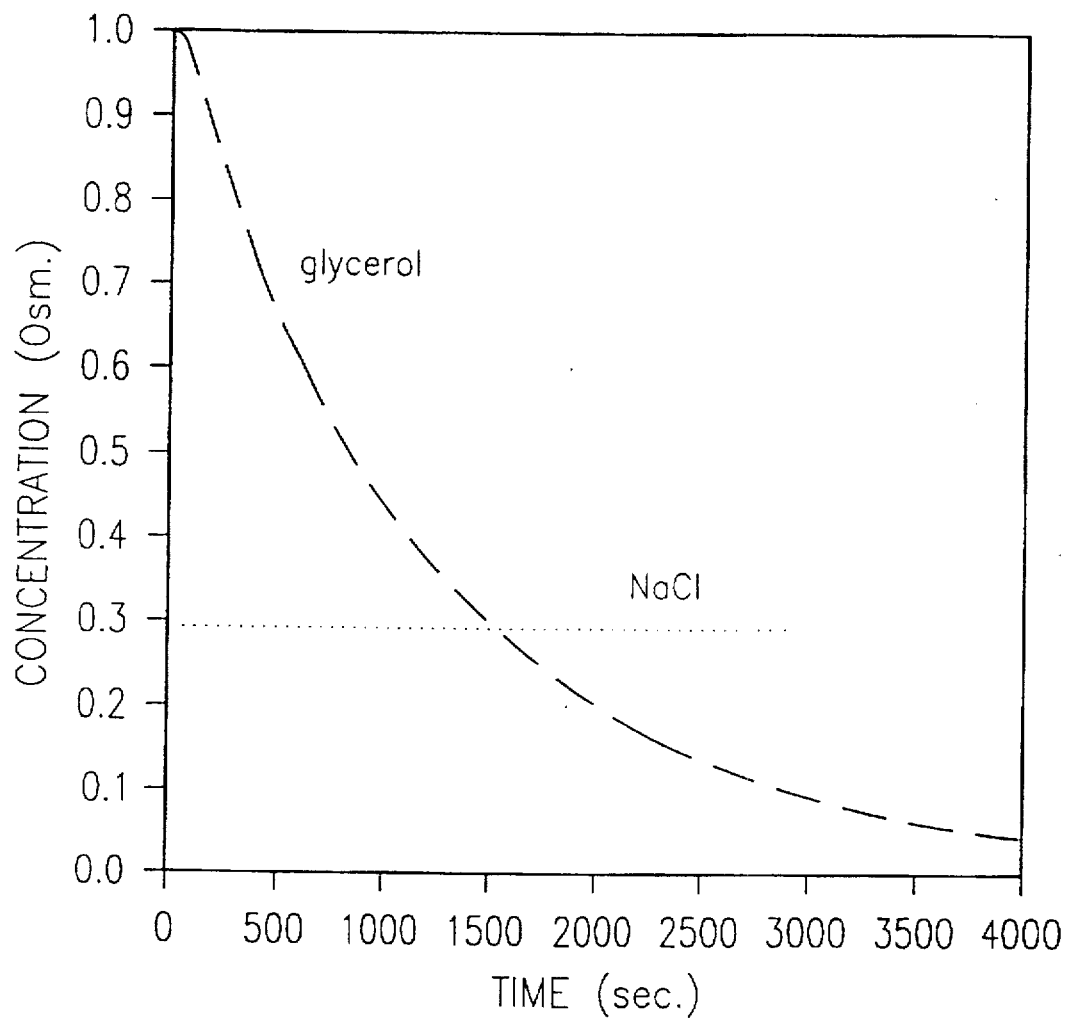
FIG. 21 is a graphical portrayal of an example of the decrease in CPA concentration around a cell-type using a membrane.
Figure 22:
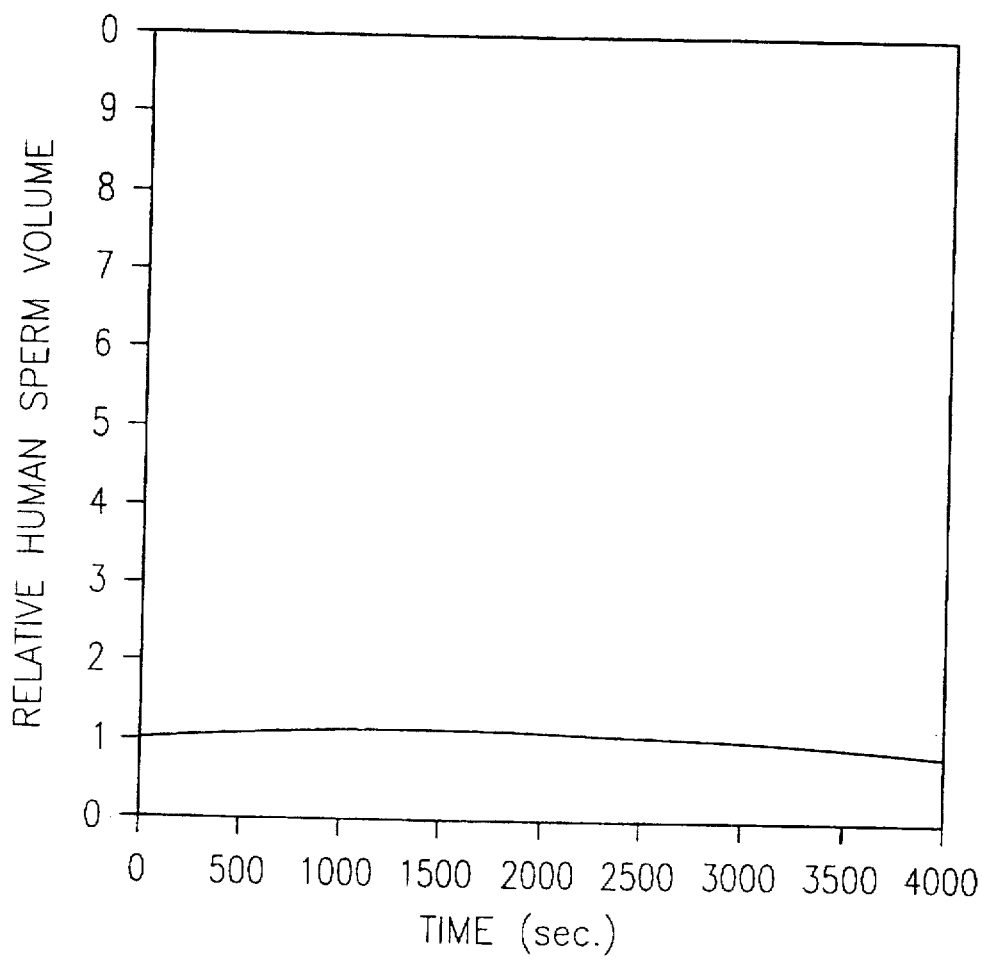
FIG. 22 is a graphical portrayal of an example cell-volume change using a membrane to remove CPA from a cell-type.

A corresponding compiler program using a finite difference method to calculate the above equations is used to simulate the mass transfer process in the system. The values of f, L2, $C_f$, $C_i$, L1, D1, D2 and $h_D$ can be used as control factors or adjustable parameters in the computer simulation. Using this computer program coupled with the computer program to calculate cell membrane transport (described by cell membrane transport equations 1 to 4, presented earlier), one may calculate the kinetic decrease of CPA concentration in the cell suspension and in cells as well as corresponding cell volume expansion. The optimal parameters to be used to design the system are simply those combinations which allow the quickest removal of the CPA but do not cause cell volume excursion beyond cell tolerance limits. One set of acceptable values of parameters for designing the diffusion washing device for human sperm was predicted from computer simulations: pore size: 0.65 μm in diameter, 70% pore area, 0.5 mm of the chamber space, i.e. L value. Calculated kinetic changes of glycerol concentration (initial 1M) at the chamber position A (center, see FIG. 19) and B (internal surface of porous membrane, see FIG. 19) are shown in FIG. 21, and the corresponding cell volume changes are calculated and predicted to be below the cell tolerance limit (1.1 times isotonic sperm volume), as shown in FIG. 22. Using a diffusion device design based on the computer simulation results above, over 95% of 1M glycerol was removed from the human sperm cells within 10 minutes without significant cell clumping, loss in motility or membrane integrity, or curling of sperm tails; this result was consistent with theoretical predictions.

Figure 23:
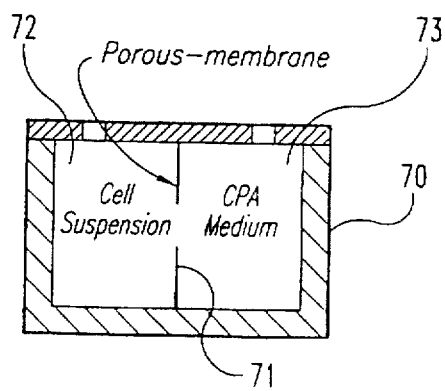
FIGS. 23 to 35 are examples of devices that can be used with a membrane that is specifically designed to add or remove CPA at a predetermined rate.

Found in this fashion, several designs of devices are possible to add or remove a cryoprotective agent in an optimal manner. A most simple design is shown in FIG. 23. The device simply consists of a body 70 separated into at least two compartments by a membrane 71. The membrane is chosen as described above. A cell suspension is placed in chamber 72 and a CPA of known concentration and temperature is placed in clamber 73. Nearly immediately, water will flow from chamber 72 through membrane 71 and into chamber 73. Simultaneously, CPA will flow from chamber 73, through membrane 71, and into chamber 72. Because of the selection of the membrane, the concentration of CPA in chamber 72 will rise at a predetermined rate that does not allow the cells in suspension to exceed the predetermined volumetric limits. A similar device can also be made for removing CPA from a cell suspension.

Figure 24:
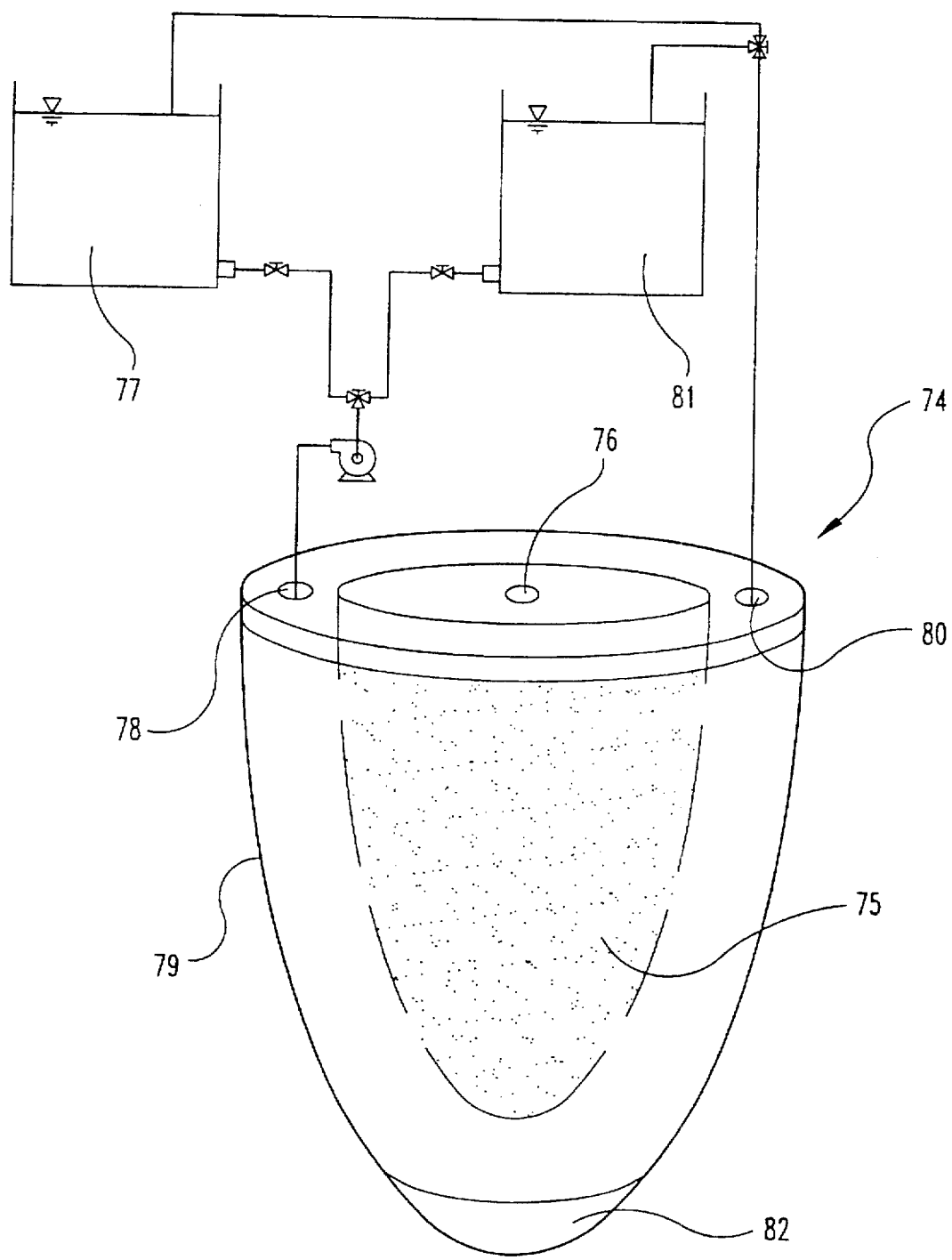

Referring next to FIG. 24, a slightly more complex device 74 is shown. The device has an inner membrane pouch 75 chosen for its ability to regulate CPA flow at a prescribed rate. A biological cell sample is inserted at inlet 76 an into pouch 75. Cryoprotectant is flowed from supply 77 into inlet 78 and between the gap area between pouch 75 and outer bag 79. The cryoprotectant entirely fills the gap area and then leaves at outlet 80 to return to supply 77. The membrane pouch 75 allows CPA to flow into the cell sample and water to flow out. The membrane is selected as discussed in this specification so that CPA does not enter the sample so quickly that the lower cell volume is exceeded. To remove CPA from the cell sample, and isotonic fluid is flowed from supply 81, into inlet 78, and allowed to fill the gap area between pouch 75 and outer bag 79. Now the membrane pouch 75 allows isotonic fluid to contact the cell sample while also allowing the CPA to flow out of the sample, through the membrane, and into the isotonic fluid stream. Again the membrane is selected as discussed in this specification, however, this time the membrane does not allow water to contact the cell sample so rapidly that the cell's upper volume limit is exceeded. To avoid thermal shock during freezing, the device may also include a seeding bar 82. The seeding bar is simply a piece of metal that is colder than the sample so that the phase transition associated with freezing begins at the seeding bar to slowly move through the sample.

Figure 25A:
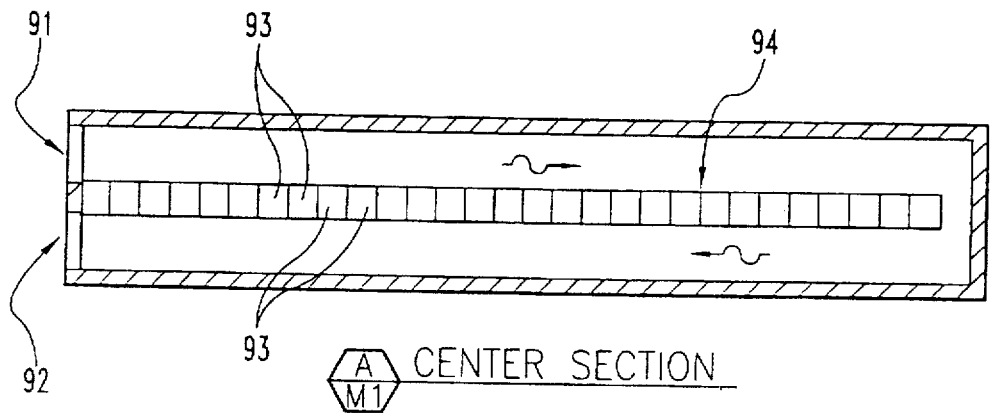
Figure 25:
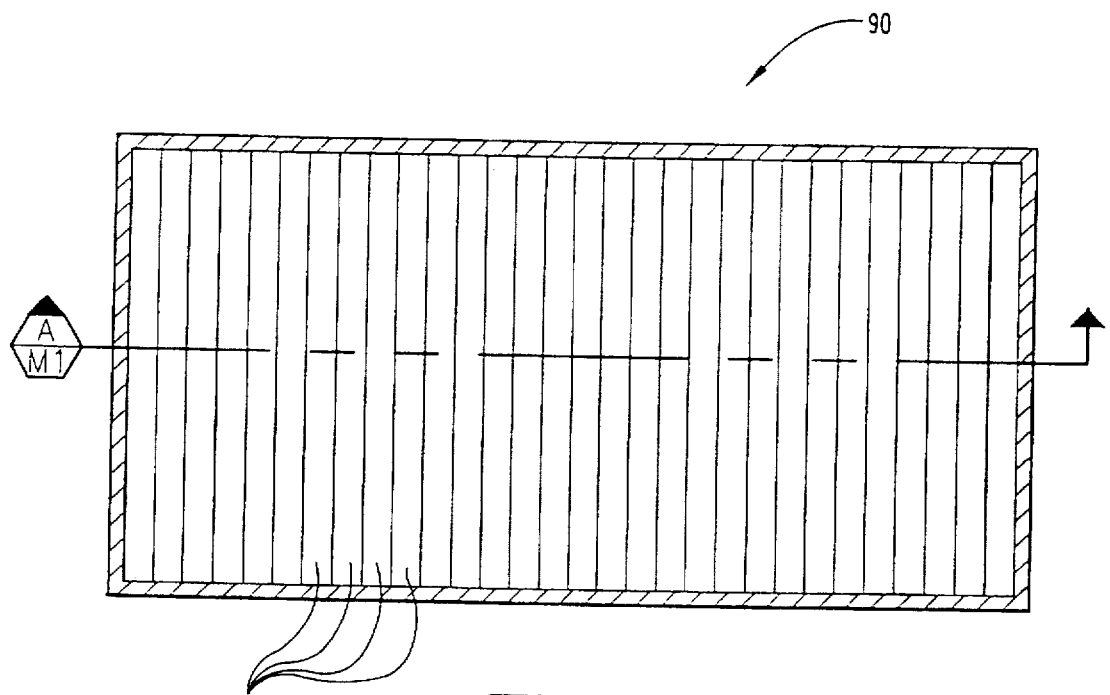
Figure 26:
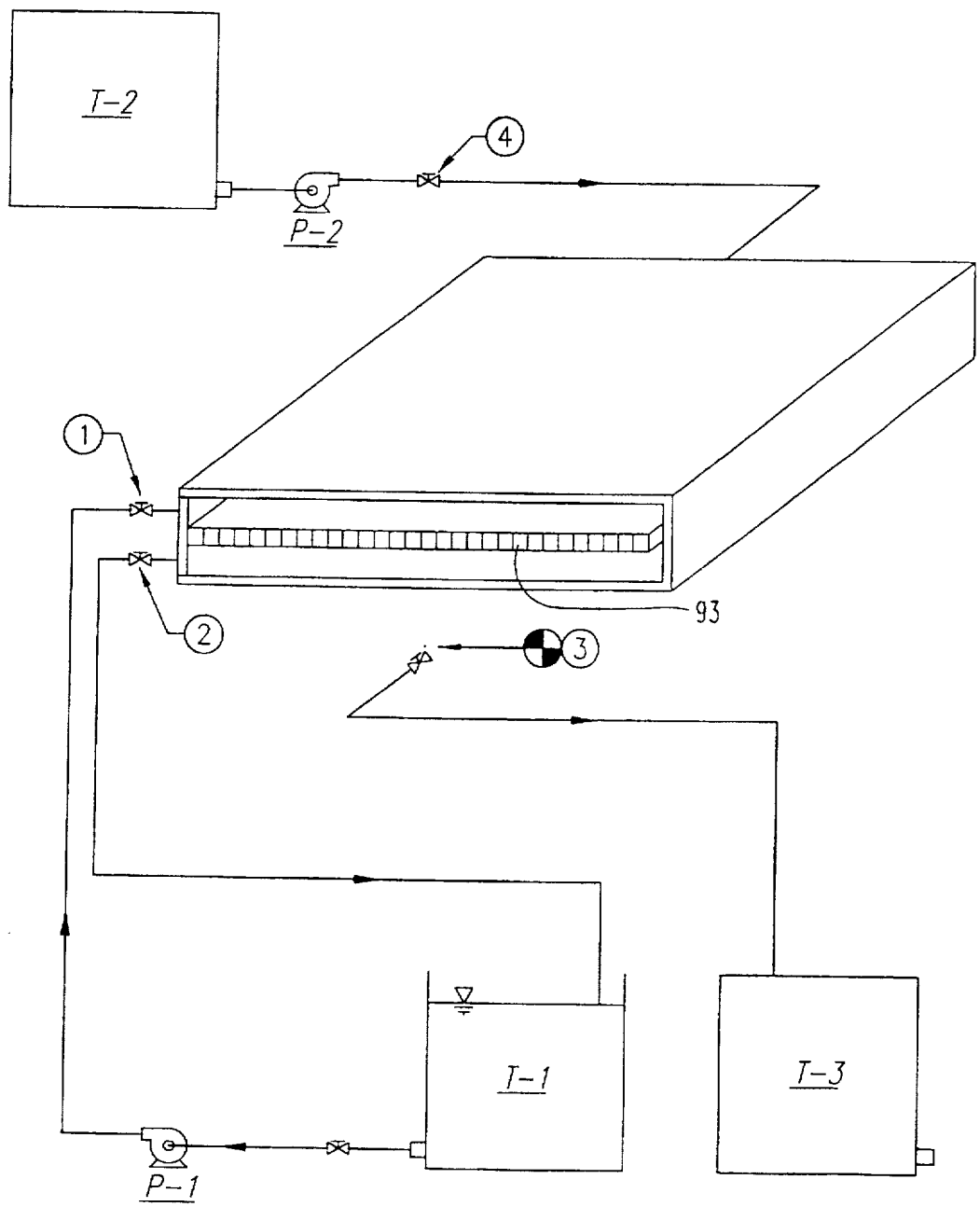

An example of another device 90 is generally shown in FIG. 25. This is a cross flow device where flow diffusion of CPA into or out of the biological cells is facilitated by flow perpendicular to that of the CPA solution or isotonic fluid. CPA enters at 91 and exits at 92. A biological cell sample is placed in compartments 93. A membrane 94 with predetermined flow characteristics separates channels 93 and the flow of CPA. Referring next to FIG. 26, the protected cells (initially rich in CPA) flow perpendicular to the page in square compartments 93. The cells are pumped from storage tank T-2 by pump P-2 through valve 4 into the device. After flowing through the device and having the CPA diffused out of the cell, the cells are allowed to flow into storage tank T-3. A solution with zero concentration CPA is pumped via pump P-1 from tank T-1 into the device. The solution flow is parallel to the sheet. The solution flows across the top of the flow compartments and then is deflected to flow along the bottom of the compartment. CPA rich solution then exits the device through valve 2. This procedure assumes that the cross flow diffusion device is used to diffuse the CPA out of the cells or tissue that has been preserved and subsequently thawed. The device also could operate to vitrify the cell with a CPA in which case a CPA rich solution is pumped from tank T-1 in through valve 1 and cells with zero concentration of CPA flow into the device.

For cell CPA removal, the diffusion rate of the CPA through the plasma membrane of the cell is highest when the solution initially enters the device through valve 1. The CPA concentration gradient is highest at this point as the cell has a high concentration of CPA and the solution contains no CPA. In order to combat the situation where the concentration gradient is lowered as the solution flows through the device is to redirect the solution to flow along the bottom of the flow compartments. The highest CPA concentration gradient for this redirected (bottom) flow occurs at the right end of the device, above which the lowest upper CPA concentration gradient exists. This redirected flow has a balancing effect on the diffusion rate of the CPA out of the cells, which is a function of the concentration gradient.

The membrane in the cross flow diffusion device is placed across the top and bottom of the many compartments that contain the flow of the protected tissue or cells. These flow compartments are separated by plastic or metal spacers which maintain the desired shape. This design allows the closing of a compartment should the membrane rupture.

Figure 27:
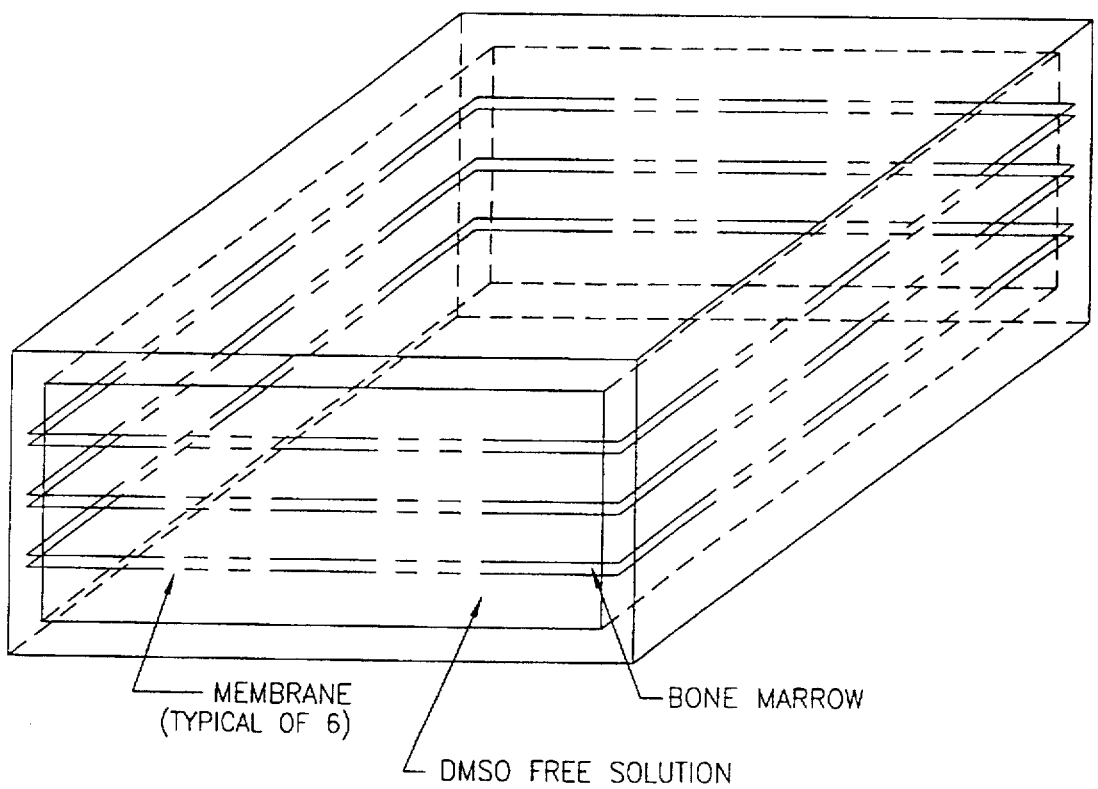
Figure 28:
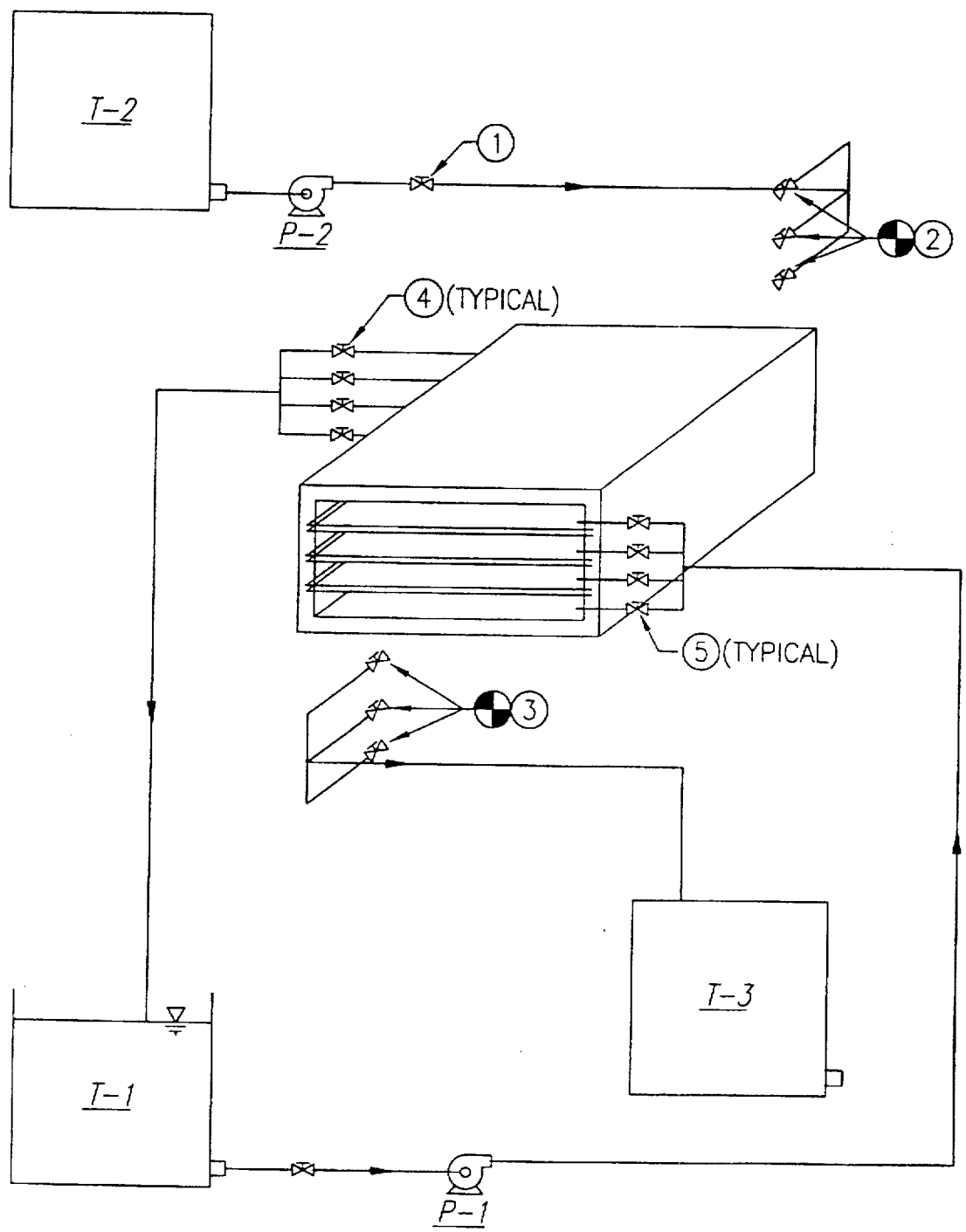
Figure 29:
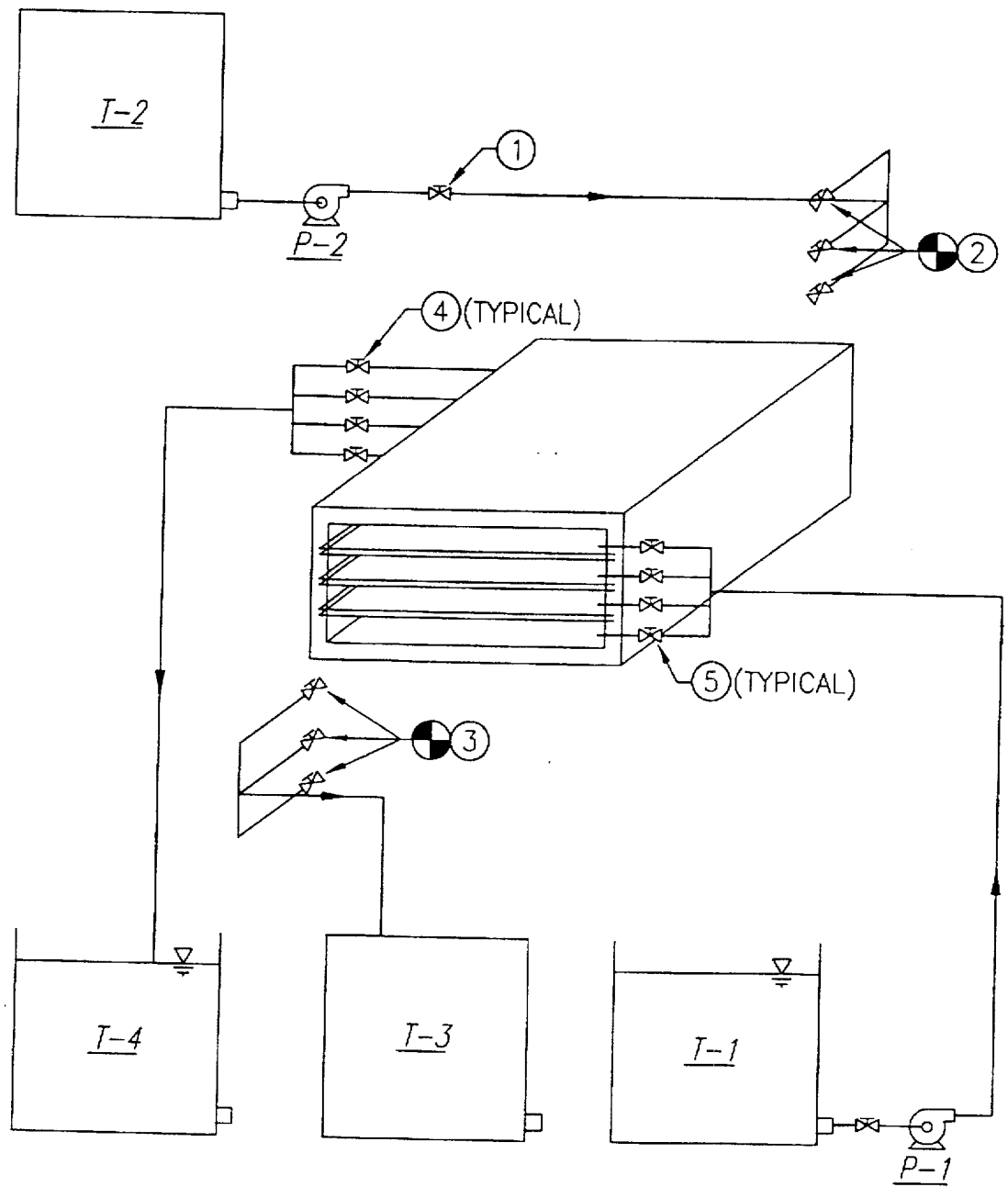

Referring to FIG. 27, a device is shown to use with counter flow diffusion. In this design, the diffusion of CPA into or out of the tissue or cells is facilitated by flowing the cells and CPA solutions in opposite directions. The flow control of this device is shown in FIG. 28. The protected cells (initially rich in CPA) flow from storage tank T-2 by pump P-2 into the device at valve 2. The cells flow in thin sheets to allow CPA to diffuse out of the cell and out of the solution containing the cells through the top or bottom membrane. A solution that initially contain no CPA is pumped into the device at the end opposite that at which the cells enter the device. This solution is pumped from tank T-1 via pump P-1 into the device through valve 4. The exiting solution, now rich in CPA, exits the device through valve 5. The cells exit the device through valve 3. FIG. 29 shows an alternate may to operate the device.

This procedure assumes that the counter flow diffusion device is used to diffuse the CPA out of the cells or tissue that has been preserved and subsequently thawed. The device could also operate to vitrify the cell with a CPA in which case a CPA rich solution is pumped from tank T-1 in through valve 1 and cells with zero concentration of CPA flow into the device.

The use of a counter flow design keeps the concentration gradient of the CPA at a high level throughout the device. The cells that enter the device initially have a high concentration of CPA as they pass through the device. The diffusion rate of CPA from the cell is maintained at a higher level than in the counter flow design since that rate is directly proportional to the concentration gradient.

The device is designed such that membrane sheets are mounted parallel to each other at a minimum distance according to the particular cell type. The most optimal design being spacing only slightly larger than one cell diameter to maximize the exposure of each individual cell.

Figure 30:
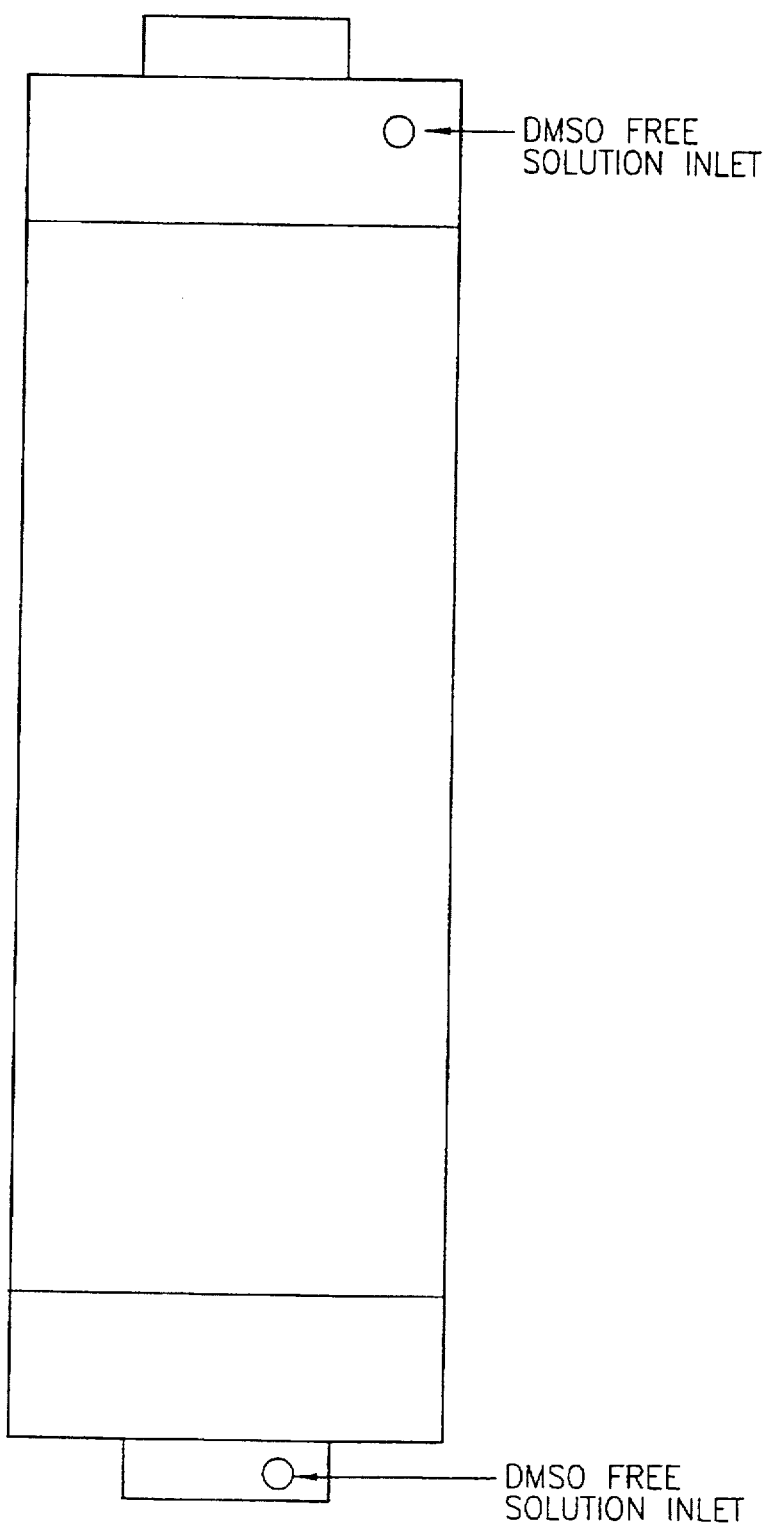
Figure 31:
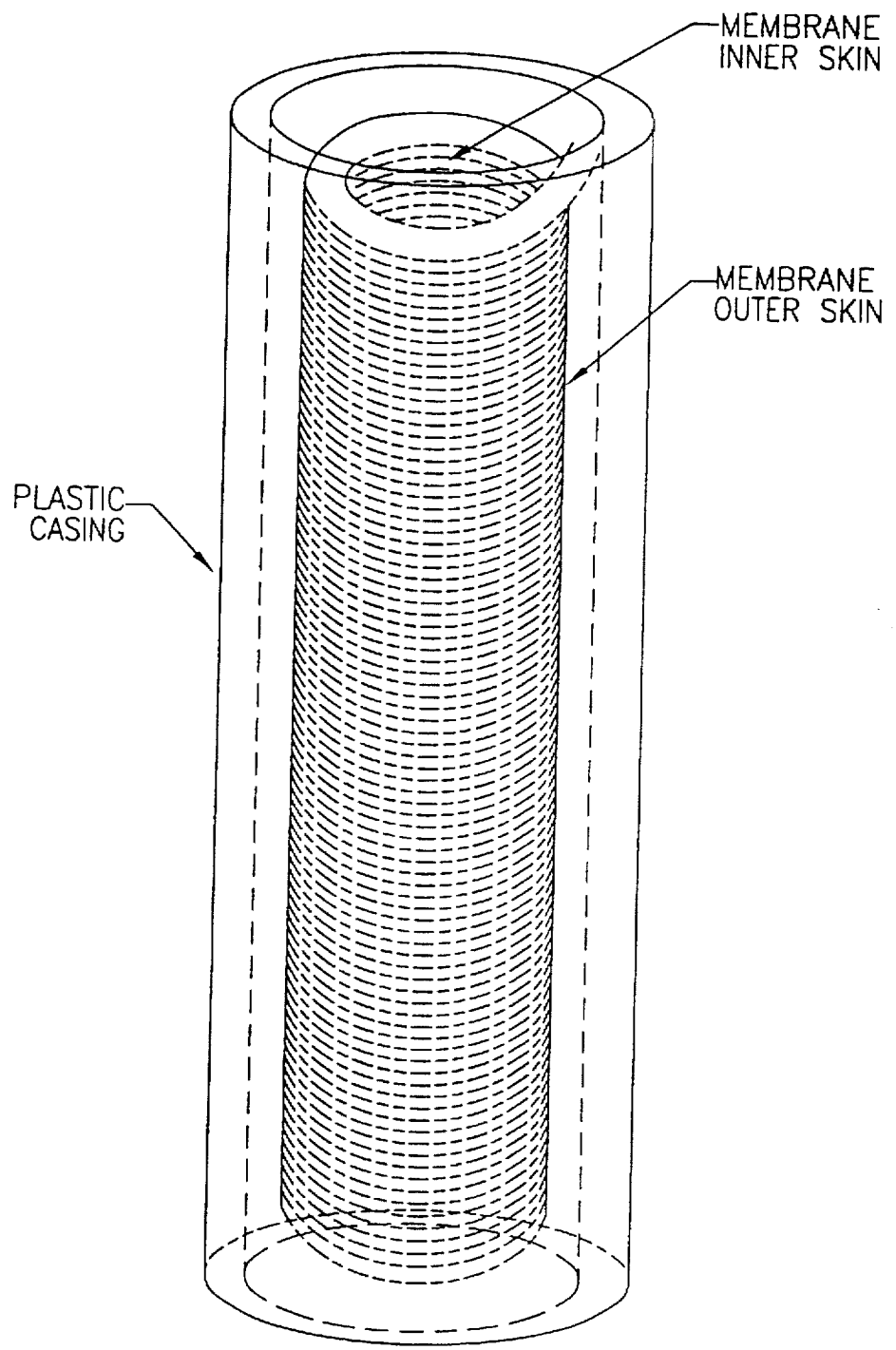
Figure 32:
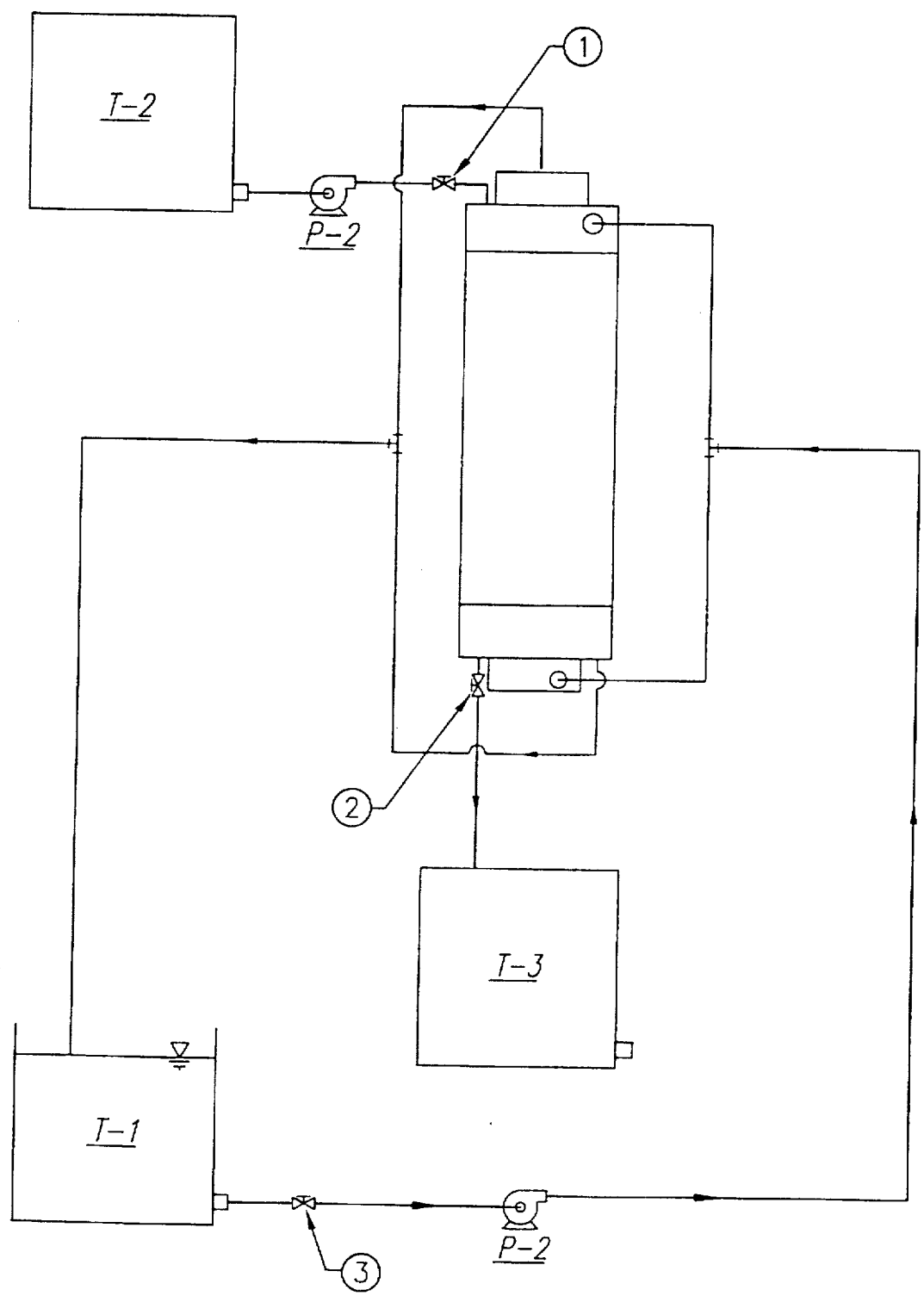

Referring next to FIGS. 30 and 31 a spiral flow device is shown. The spiral flow diffusion device facilitates the diffusion of the CPA into or out of the tissue or cells by utilizing a design where protected cell flow is subjected to both an inner and outer CPA solution flow. Referring next to FIG. 32, the cells initially with a CPA concentration enter the device from tank T-2 through the top of the device at valve 1. The spiral design allows the cells to proceed through the device using only gravity. The CPA free solution is pumped into the top and bottom of the device by pump P-1. The CPA free solution that enters from the bottom of the device is pumped up through the center of the device. The remaining CPA solution is pumped down around the outer spiral cylinder. After the cells have completed their spiral path through the device, they exit through valve 2. The solution which now contains a concentration of CPA exits the device through the top and bottom valves.

The procedure assumes that the spiral flow diffusion device is used to diffuse the CPA out of the cells or tissue that has been preserved and subsequently thawed. The device also could operate to vitrify the cell with a CPA in which case a CPA rich solution is pumped from tank T-1 and cells with zero concentration of CPA flow into the device.

The use of the spiral design typical allows for the cells to travel over a greater distance than the previously presented devices thereby increasing the area over which diffusion may occur. Pump one may be eliminated from the design by having the cells gravity feed down the spiral insert. The fact that the design contains two inlets and two outlets for the CPA solution assures that a high concentration gradient is maintained in the device. This has a positive effect of the diffusion rate of the CPA.

The spiral design is such that a membrane sheet is attached to the inside and outside surface of the spiral structure. This allows for easy membrane removal and replacement.

Figure 33:
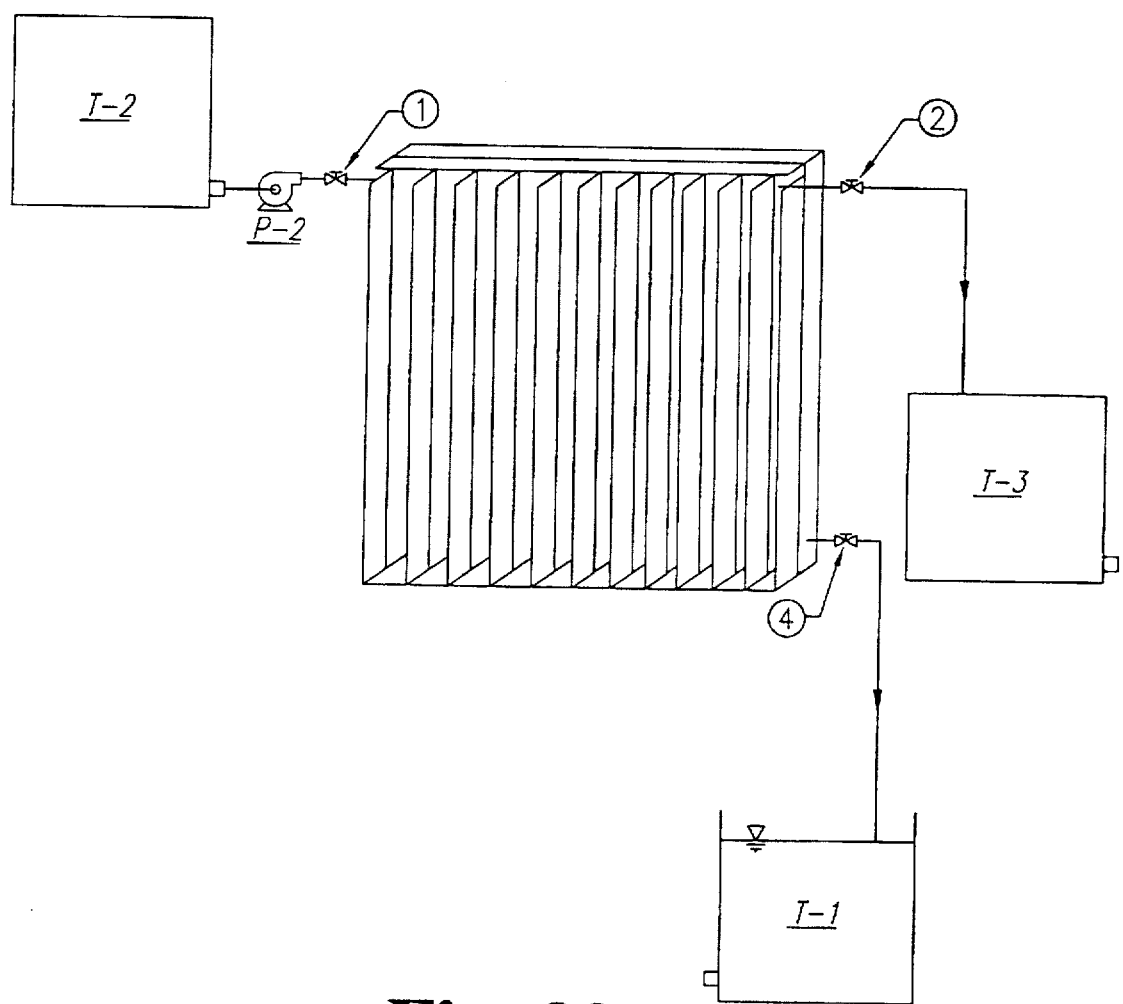
Figure 34:
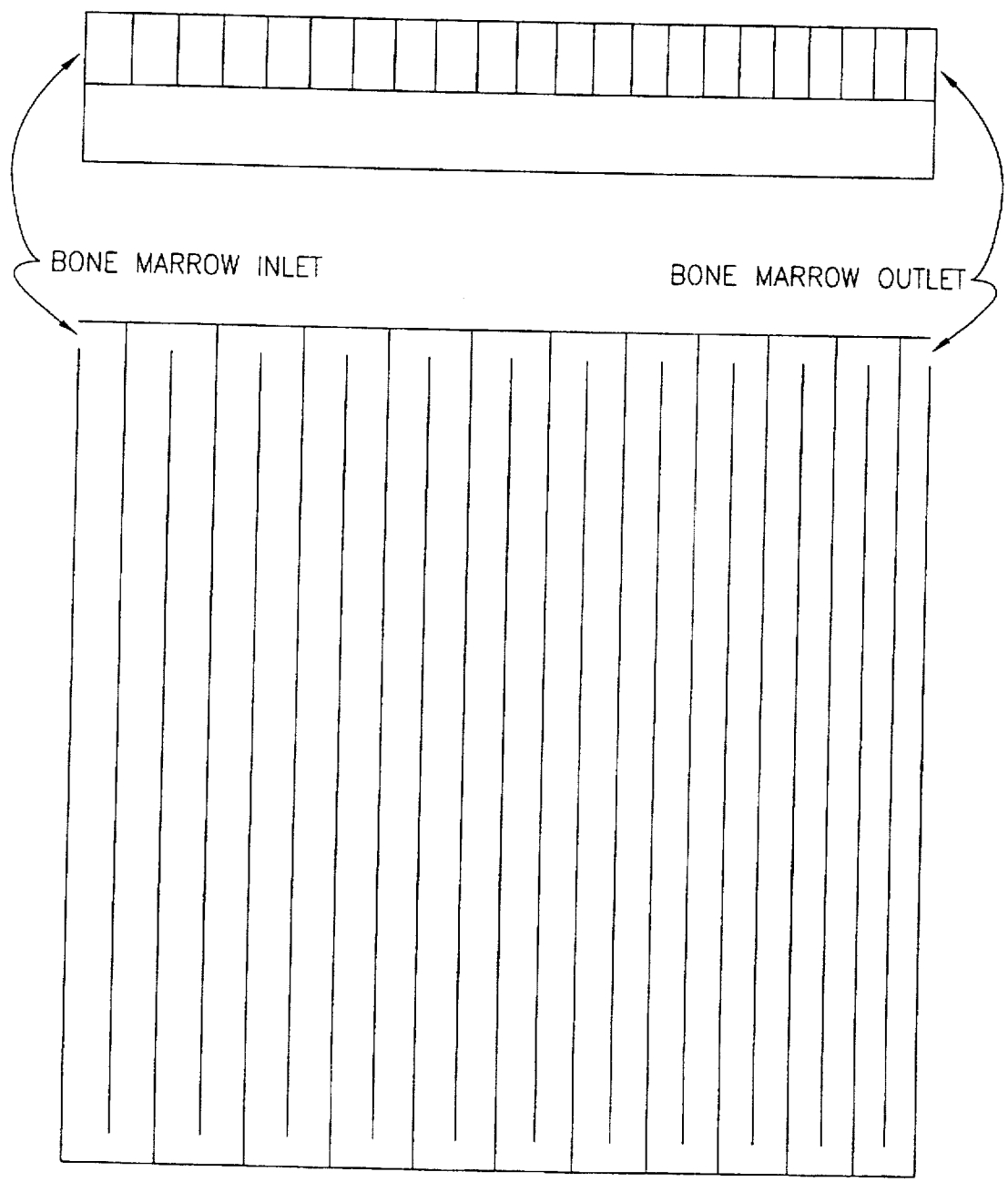

Referring next to FIGS. 33 and 34, a reverse osmosis device is shown that utilizes the principles of this invention. The reverse osmosis diffusion device facilitates the diffusion of CPA out of the protected tissue or cells by passing a solution containing the cells through a membrane permeable only to CPA. Referring to FIG. 33, the protected cells in tank T-2 are to be diluted with a solution to aid in their transport through the device. This solution should be a biologically harmless agent in the event that some residue remains with the cells. The solution is pumped into the device at valve 1 by pump P-2. The solution is forced upon a membrane that is permeable only to the CPA and the solution, but does not allow the cells to pass. The pressure needed to force the solution through this membrane is provided in part by pump P-2. Additional back pressure on the solution is provided by decreasing the flow area as the solution passes through the device. The cells exit the device through valve 2 and empty into tank T-3. The CPA solution exits the device through valve 4.

The reverse osmosis device would be effective in removing a nonpermeating CPA from a cell solution. The device removes the CPA from the protected cell solution by subjecting the solution to a membrane rather than relying on the passive transport of the CPA as in the other designs.

Figure 35:
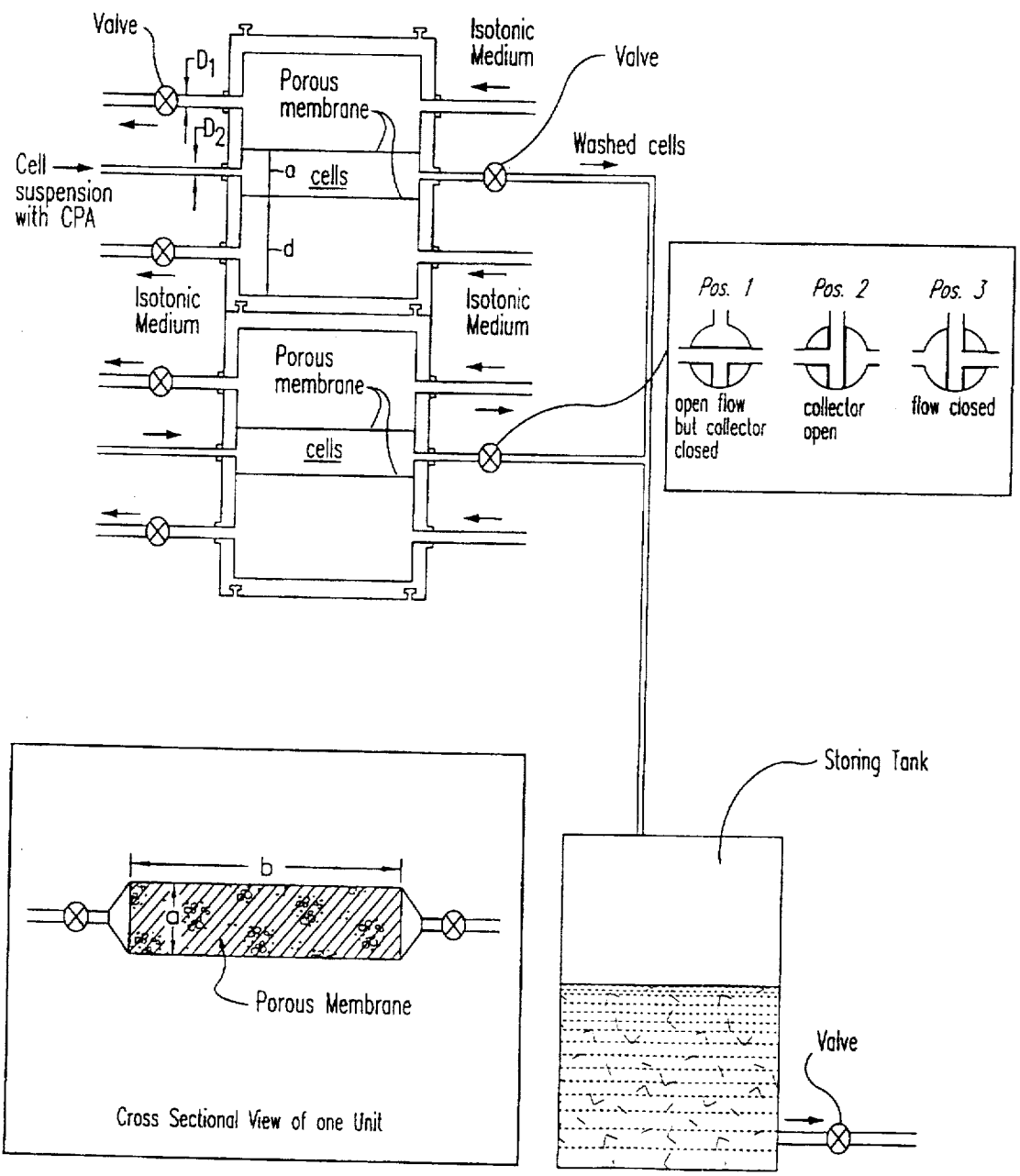

Finally, FIG. 35 shows how two or more of the devices contemplated by this invention may be arranged to operate in parallel fashion.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

We claim:

1. A method to add cryoprotectant to the cells of an animal species comprising:
   a) predetermining a lower cellular volume limit below which a user-defined fraction of cells lose their viability,
   b) selecting a first concentration of cryoprotectant solution,
   c) calculating whether said first concentration of cryoprotectant solution will cause the cells to shrink below the lower cellular volume limit by a calculation which uses the water permeability coefficient and the cryoprotectant permeability coefficient of the cell, repeating steps b) and c) as necessary in order to calculate a predetermined concentration of cryoprotectant solution which will permit increasing of the concentration of cryoprotectant in the cells while still maintaining the viability of a user-defined fraction of the cells,
   d) contacting said cells with the solution of the predetermined concentration of cryoprotectant.

2. The method of claim 1, wherein said lower cellular volume limit is predetermined by shrinking said cells of said animal species in increasingly hypertonic conditions until a user-defined fraction of said cells lose their viability.

3. The method of claim 2, wherein said cells are sperm cells and said viability is measured by analysis of sperm motility.

4. The method of claim 1, wherein said cryoprotectant comprises glycerol.

5. The method of claim 1, wherein said contacting comprises contacting said cells with the cryoprotectant solution in two or more substantially constant volumes.

6. The method of claim 1, wherein said contacting comprises contacting said cells with the cryoprotectant solution in two or more volumes wherein said volumes increase the level of cryoprotectant in the cells by substantially constant increments in molarity.

7. The method of claim 1, wherein said cells are sperm cells and said cellular volume limit is about 75% of the isotonic volume of said sperm cells.

8. The method of claim 1, wherein said cells are blood cells.

9. The method of claim 1, wherein said cells are pancreatic islet cells.

10. The method of claim 1, wherein steps (b), (c) and (d) are repeated for a second concentration of cryoprotectant that is higher than said first concentration.

11. A method to add cryoprotectant to the cells of an animal species comprising:
   a) predetermining a lower cellular volume limit below which a user-defined fraction of cells lose their viability,
   b) selecting a first rate of cryoprotectant addition,
   c) calculating whether said first rate of cryoprotectant addition will cause the cells to shrink below the lower cellular volume limit by a calculation which uses the water permeability coefficient and the cryoprotectant permeability coefficient of the cell, repeating steps b) and c) as necessary in order to calculate a predetermined rate of cryoprotectant solution addition while still maintaining the viability of a user-defined fraction of the cells,
   d) contacting said cells containing cryoprotectant with a first solution of cryoprotectant and continually increasing the cryoprotectant concentration in the solution at the predetermined rate.

12. The method of claim 11, wherein said lower cellular volume limit is predetermined by shrinking said cells of said animal species in increasingly hypertonic conditions until a predetermined fraction of said cells lose their viability.

13. The method of claim 12, wherein said cells are sperm cells and said viability is measured by analysis of sperm motility.

14. The method of claim 11, wherein said cryoprotectant is selected from the group consisting of dimethyl sulfoxide, glycerol, and ethylene glycol.

15. The method of claim 11, wherein said continually increasing step is performed with a porous membrane that separates said first solution and a second solution, said membrane regulating the the flow of cryoprotectant and water between said first and second solutions.

16. The method of claim 15, wherein said second solution begins with a cryoprotectant concentration that is higher than the cryoprotectant concentration of the first solution.

17. The method of claim 11, wherein said cells are blood cells.

18. The method of claim 11, wherein said cells are pancreatic islet cells.

19. A method to add cryoprotectant to the cells of an animal species, comprising:
   contacting said cells with one or more stepwise additions of aliquots containing said cryoprotectant, wherein each aliquot has a predetermined concentration of said cryoprotectant that is higher than the cryoprotectant concentration within the cells with which it is contacted, said predetermined concentration substantially preventing the volumetric excursion of said cells beyond a predetermined lower cellular volume limit, and said predetermined concentration being predetermined by determining the cellular volume of said animal cells for a given concentration of said cryoprotectant with differential equations:

$$J_v = 1/A_c \, dV(t)/dt$$
$$= -L_p\{(C^e_{salt} - C^i_{salt}) + \sigma(C^e_{CPA} - C^i_{CPA})\}$$

-continued $$J_{CPA} = 1/A_c \, dN_{CPA}/dt$$
$$= \bar{C}_{CPA}(1-\sigma)J_v + P_{CPA}(C^e_{CPA} - C^i_{CPA})RT$$

$$C^i_{salt}(t) = C^{e,o}_{salt}\{(V(0) - V_b - \bar{V}_{CPA}N^{i,o}_{CPA})/(V(t) - V_b - \bar{V}_{CPA}N^i_{CPA}(t))\}$$

$$C^i_{CPA}(t) = [N^i_{CPA}(t)]/[V(t) - V_b - \bar{V}_{CPA}N^i_{CPA}(t)]$$

wherein $J_v$=total volume flux, V=cell volume, t=time, N=mole number of the solute, $A_c$=cell surface area, $L_p$=water permeability coefficient, C=concentration of solute, $J_{CPA}$=cryoprotectant flux across the cell membrane, superscript e=extracellular, superscript i=intracellular, $\bar{C}_{CPA}$=average cryoprotectant concentration of extracellular and intracellular concentrations, R=gas constant, T= absolute temperature, $P_{CPA}$=cryoprotectant permeability coefficient of the animal cell, $\sigma$=the reflection coefficient of said cryoprotectant, wherein $V_b$=osmotically-inactive cell volume, $\bar{V}_{CPA}$=partial mole volume of said cryoprotectant, 0=initial condition; and determining the size of said cellular volume relative to said predetermined lower cellular volume limit.

20. The method of claim 19, wherein said cells are sperm cells.

21. The method of claim 19, wherein said cells are blood cells.

22. The method of claim 19, wherein said cells are pancreatic islet cells.

23. The method of claim 19, wherein said cryoprotectant is selected from the group consisting of dimethyl sulfoxide, glycerol, and ethylene glycol.

24. A method to add cryoprotectant to the cells of an animal species, comprising:
   contacting said cells with a first solution of cryoprotectant and continually increasing the concentration of said cryoprotectant in said first solution at a predetermined rate, said predetermined rate substantially preventing the volumetric excursion of said cells beyond a predetermined lower cellular volume limit, and said predetermined rate being predetermined by determining the cellular volume of said animal cells for a given concentration of said cryoprotectant with differential equations:

$$J_v = 1/A_c \, dV(t)/dt$$
$$= -L_p\{(C^e_{salt} - C^i_{salt}) + \sigma(C^e_{CPA} - C^i_{CPA})\}$$

$$J_{CPA} = 1/A_c \, dN_{CPA}/dt$$
$$= \bar{C}_{CPA}(1-\sigma)J_v + P_{CPA}(C^e_{CPA} - C^i_{CPA})RT$$

$$C^i_{salt}(t) = C^{e,o}_{salt}\{(V(0) - V_b - \bar{V}_{CPA}N^{i,o}_{CPA})/(V(t) - V_b - \bar{V}_{CPA}N^i_{CPA}(t))\}$$

$$C^i_{CPA}(t) = [N^i_{CPA}(t)]/[V(t) - V_b - \bar{V}_{CPA}N^i_{CPA}(t)]$$

wherein $J_v$=total volume flux, V=cell volume, t=time, N=mole number of the solute, $A_c$=cell surface area, $L_p$=water permeability coefficient, C=concentration of solute, $J_{CPA}$=cryoprotectant flux across the cell membrane, superscript e=extracellular, superscript i=intracellular, $\bar{C}_{CPA}$=average cryoprotectant concentration of extracellular and intracellular concentrations, R=gas constant, T=absolute temperature, $P_{CPA}$=cryoprotectant permeability coefficient of the animal cell, $\sigma$=the reflection coefficient of said cryoprotectant, wherein $V_b$=osmotically-inactive cell volume, $\bar{V}_{CPA}$=partial mole volume of said cryoprotectant, 0=initial condition; and determining the size of said cellular volume relative to said predetermined lower cellular volume limit.

25. The method of claim 24, wherein said cells are sperm cells.

26. The method of claim 24, wherein said cells are blood cells.

27. The method of claim 24, wherein said cells are pancreatic islet cells.

28. The method of claim 24, wherein said cryoprotectant is selected from the group consisting of dimethyl sulfoxide, glycerol, and ethylene glycol.

* * * * *

UNITED STATES PATENT AND TRADEMARK OFFICE
CERTIFICATE OF CORRECTION

PATENT NO. : 5,753,427  
DATED : May 19, 1998  
INVENTOR(S) : Critser, et al

Page 1 of 4

It is certified that error appears in the above-identified patent and that said Letters Patent is hereby corrected as shown below:

On the title page,
  In item 57 of the title page, line 9, please change "cells" to --cells'--.

In col. 1, line 60, please change "ethleneditrotetra" to --ethlenedinitrotetra--.

In col. 2, line 64, please change "riot" to --not--.

In col. 4, line 42, please change "cellos" to --cell's--.

In col. 6, line 1, please change "my" to --by--.

In col. 7, line 1, please change first occurrence of "$V_{cpa}$" to --$\overline{V}_{cpa}$--.

In col. 7, line 9, please insert a comma after "V(O)".

In col. 8, line 26, please change "and" to --an--.

In col. 8, line 63, please change "Camber" to --Chamber--.

In col. 9, line 36, please change "human" to --Human--.

In col. 10, line 10, after "(i-1)" please insert --$M_f$"--.

UNITED STATES PATENT AND TRADEMARK OFFICE
CERTIFICATE OF CORRECTION

PATENT NO. : 5,753,427
DATED : May 19, 1998
INVENTOR(S) : Critser, et al

It is certified that error appears in the above-identified patent and that said Letters Patent is hereby corrected as shown below:

In col. 10, line 49, please change "Polarity" to --molarity--.

In col. 10, line 54, please delete the period.

In col. 14, line 65, please change "stimulation" to --simulation--.

In col. 16, line 14, please change "EMS" to --FMS--.

In col.16, line 22, please change "and," second occurrence, to --an--.

In col. 18, line 60, please change "warning" to --warming--.

In col.18, line 66, please change "tie" to --the--.

In col. 19, line 17, please change "effected" to --affected--.

In col. 19, line 49, please change "riot" to --not--.

In col. 21, line 5, please change "compiler" to --computer--.

UNITED STATES PATENT AND TRADEMARK OFFICE
CERTIFICATE OF CORRECTION

PATENT NO. : 5,753,427
DATED : May 19, 1998
INVENTOR(S) : Critser, et al

It is certified that error appears in the above-identified patent and that said Letters Patent is hereby corrected as shown below:

In col. 21, line 54, please change "an" to --and--.

In col. 21, line 63, please change "and" to --an--.

In col. 23, line 4, please change "may" to --way--.

In col. 23, line 54, please change "of" to --on--.

In col. 24, line 64, insert --lower-- after "said".

In col. 25, line 3, please delete "(b), (c) and (d)." and replace with --(b) and (c)--.

In col. 25, line 5, please change "higher" to --less dilute--.

In col. 25, line 39, please delete "the," second occurrence.

UNITED STATES PATENT AND TRADEMARK OFFICE
CERTIFICATE OF CORRECTION

PATENT NO. : 5,753,427
DATED : May 19, 1998
INVENTOR(S) : Critser, et al

It is certified that error appears in the above-identified patent and that said Letters Patent is hereby corrected as shown below:

In col. 26, lines 5 and 6, please change "$V_{cpa}$" to $-\overline{V}_{cpa}$".

In col. 26, lines 50 and 51, please change "$V_{cpa}$" to $-\overline{V}_{cpa}$".

Signed and Sealed this

Second Day of March, 1999

Attest:

*Attesting Officer*

Q. TODD DICKINSON

*Acting Commissioner of Patents and Trademarks*